United States Patent
Miyazawa

(10) Patent No.: US 10,204,434 B2
(45) Date of Patent: Feb. 12, 2019

(54) INFORMATION PROCESSING APPARATUS FOR MEDICAL INFORMATION, X-RAY IMAGING APPARATUS, INFORMATION PROCESSING SYSTEM FOR MEDICAL INFORMATION, INFORMATION PROCESSING METHOD, AND RECORDING MEDIUM

(71) Applicant: CANON KABUSHIKI KAISHA, Tokyo (JP)

(72) Inventor: Nobu Miyazawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 263 days.

(21) Appl. No.: 14/931,494

(22) Filed: Nov. 3, 2015

(65) Prior Publication Data

US 2016/0133012 A1    May 12, 2016

(30) Foreign Application Priority Data

Nov. 8, 2014  (JP) .................................. 2014-227617

(51) Int. Cl.
| | |
|---|---|
| G06K 9/00 | (2006.01) |
| G06T 11/60 | (2006.01) |
| G06T 7/00 | (2017.01) |
| G06F 19/00 | (2018.01) |

(52) U.S. Cl.
CPC ............ *G06T 11/60* (2013.01); *G06F 19/321* (2013.01); *G06T 7/0012* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 6,540,680 B1* | 4/2003 | Kurosaki | A61B 8/463 600/443 |
| 2002/0122578 A1 | 9/2002 | Akahori | |
| 2005/0108060 A1* | 5/2005 | Sasano | G06Q 50/24 705/3 |
| 2007/0127793 A1* | 6/2007 | Beckett | G06T 7/0012 382/128 |
| 2011/0110496 A1* | 5/2011 | Foos | A61B 6/4405 378/98.5 |

(Continued)

FOREIGN PATENT DOCUMENTS

JP          2007-013371 A       1/2007

*Primary Examiner* — Matthew Bella
*Assistant Examiner* — Jose M Torres
(74) *Attorney, Agent, or Firm* — Canon U.S.A., Inc. IP Division

(57) ABSTRACT

An information processing apparatus for medical information includes a determination unit that determines whether specific information is to be associated with a medical image obtained by imaging of an object based on information concerning the imaging of the object, a period obtaining unit that obtains information indicating a period that has elapsed between a reference time concerning the specific information and a time of imaging of the medical image, and a processing unit that associates with the medical image the information indicating the period as the specific information in a case where the determination unit determines that the specific information is to be associated with the medical image.

18 Claims, 21 Drawing Sheets

(56) References Cited

U.S. PATENT DOCUMENTS

| | | | | |
|---|---|---|---|---|
| 2012/0183188 A1* | 7/2012 | Moriya | ............... | G06F 19/321 |
| | | | | 382/128 |
| 2013/0290024 A1* | 10/2013 | Kawanaka | .......... | G06F 19/3487 |
| | | | | 705/3 |
| 2015/0025359 A1* | 1/2015 | Fenchel | ............... | A61B 6/037 |
| | | | | 600/411 |

* cited by examiner

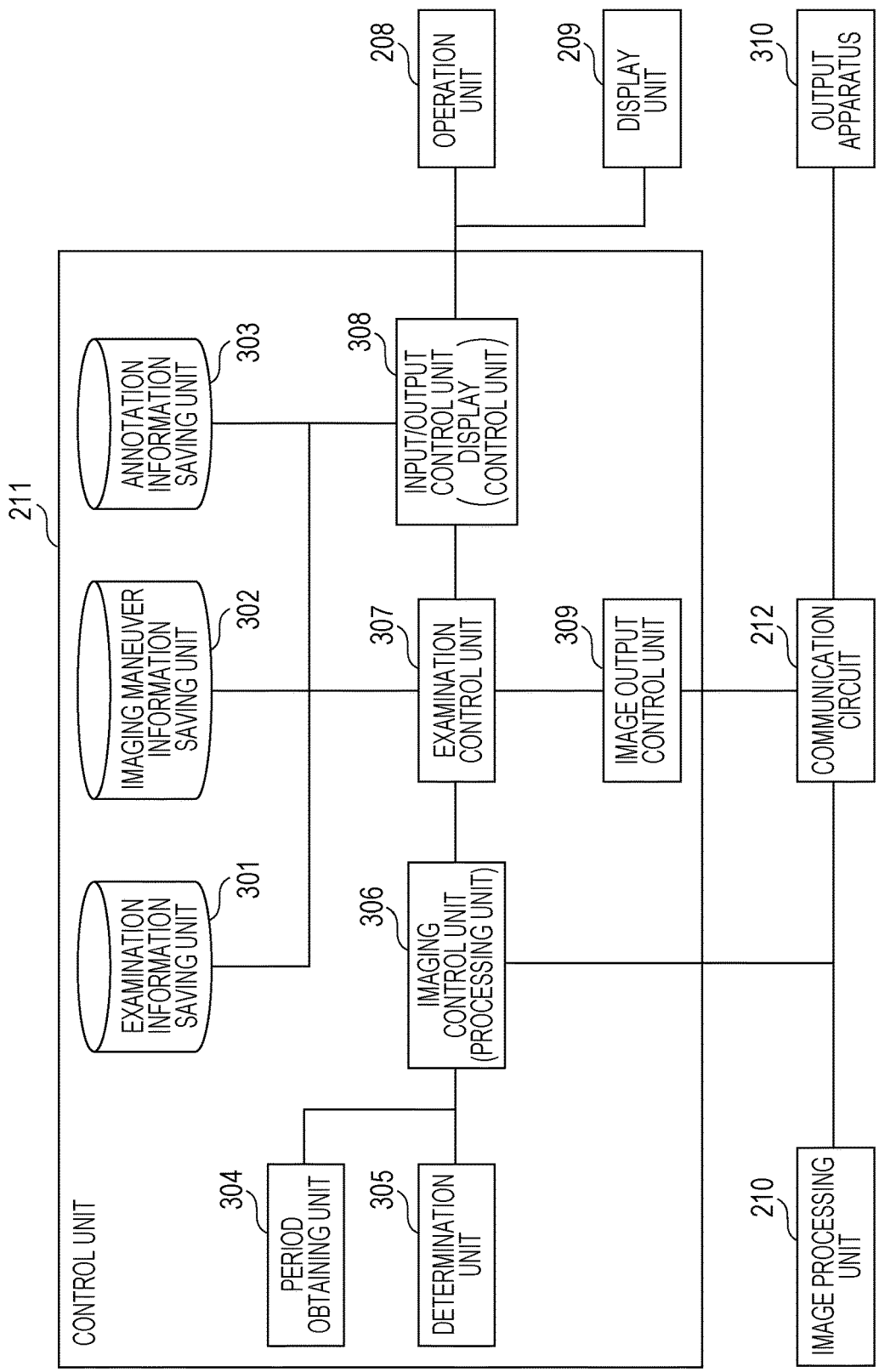

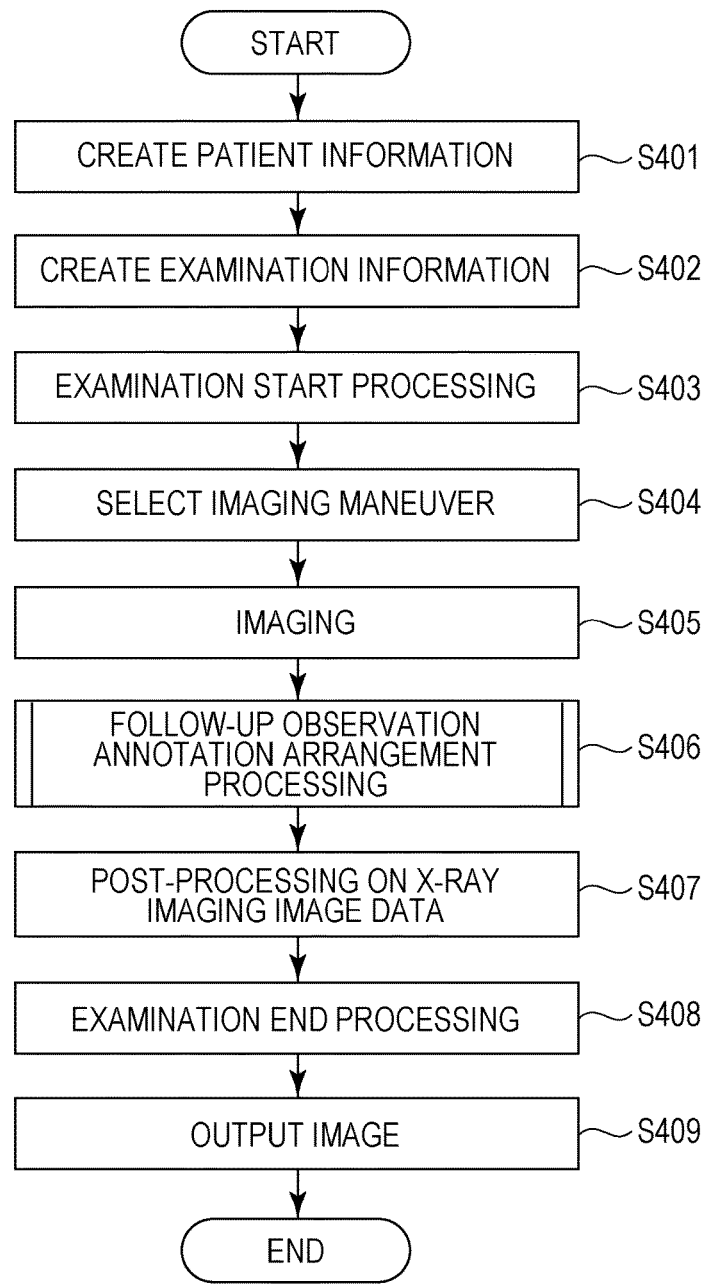

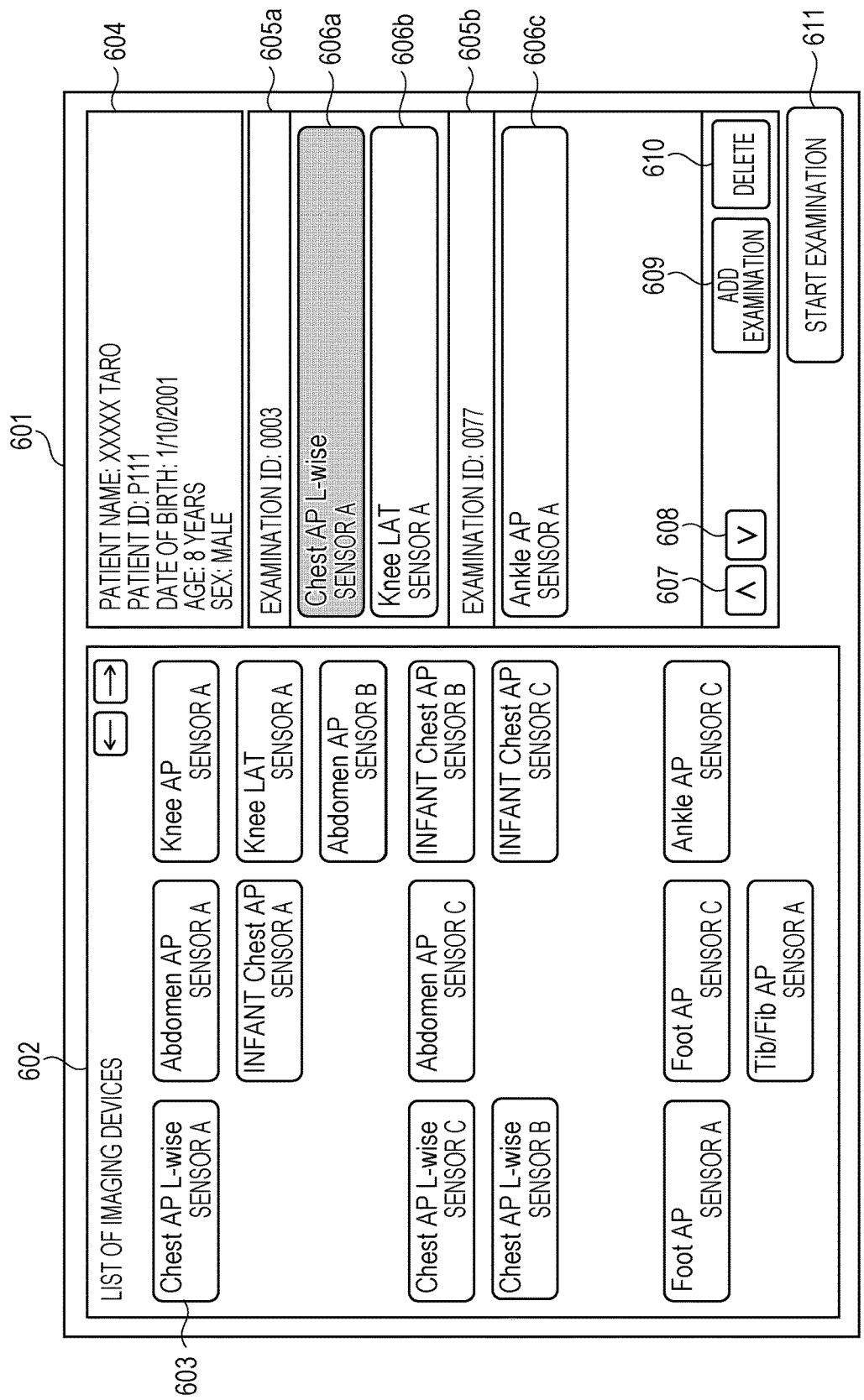

FIG. 11A

ANNOTATION SETTING — 1101

- 1102 — FONT SETTING: HG GOTHIC E ∨ | 36 ∨
- 1103 — ARRAY SYSTEM: 6 ∨ ROWS | 3 ∨ COLUMNS

| ANNOTATION CHARACTER STRING | FOLLOW-UP OBSERVATION SETTING |
|---|---|
| POST-OPERATION MINUTES | ○ |
| POST-OPERATION HOURS | ○ |
| POST-OPERATION WEEKS | ○ |
| POST-OPERATION MONTHS | ○ |
| ELAPSED HOURS | ○ |
| ELAPSED MINUTES | ○ |
| ABC | |
| DEF | |
| GHI | |
| JKL | |
| | |
| | |

1104

ADD (1105) | EDIT (1106) | DELETE (1107) | ∧ (1108) | ∨ (1109) | CANCEL (1110) | CONFIRM (1111)

FIG. 11B

ANNOTATION — 1112

ANNOTATION: POST-OPERATION MONTHS — 1113

FOLLOW-UP OBSERVATION (1114) | CANCEL (1115) | OK (1116)

FIG. 12

```
                                              1206            1201
┌──────────────────────────────────────────────────────────────────┐
│  IMAGING MANEUVER SETTING                                        │
│                                                                  │
│  PROTOCOL NAME:  [AbdomenAP]    DICOM ATTRIBUTE --------------   │
│  SERIES DESCRIPTION: [      ]   EXAMINATION REGION: [ABDOMEN ▽]  │
│  COMMENT:            [      ]   PATIENT DIRECTION:  [R/F     ▽]  │
│  LATERALITY MARKER:             POSITION OF FIELD OF VIEW:[AP ▽] │
│    L                            LATERALITY:         [U       ▽]  │
│      ARRANGEMENT POSITION:                                       │
│        [MIDDLE - CENTRAL ▽]                                      │
│        ☐ EMBED UPON IMAGING                                      │
│    R                          ANNOTATION:                        │
│      ARRANGEMENT POSITION:      ☐ EMBED ELAPSED PERIOD           │
│        [MIDDLE - CENTRAL ▽]        ANNOTATION                    │
│        ☐ EMBED UPON IMAGING                                      │
│                               ELAPSED PERIOD CHARACTER STRING:   │
│                                 [POST-OPERATION WEEKS ▽]         │
│                               ARRANGEMENT POSITION:              │
│                                 [TOP - LEFT          ▽]          │
│                                                                  │
│                                        [CANCEL] [CONFIRM]        │
└──────────────────────────────────────────────────────────────────┘
```

1202 PROTOCOL NAME  
1203 SERIES DESCRIPTION  
1204 COMMENT  
1205 LATERALITY MARKER  
1206 DICOM ATTRIBUTE  
1207 ANNOTATION  
1208 CANCEL  
1209 CONFIRM

INFORMATION PROCESSING APPARATUS FOR MEDICAL INFORMATION, X-RAY IMAGING APPARATUS, INFORMATION PROCESSING SYSTEM FOR MEDICAL INFORMATION, INFORMATION PROCESSING METHOD, AND RECORDING MEDIUM

BACKGROUND

Field

The disclosure of the present specification relates to information processing for associating supplementary information with a medical image.

Description of the Related Art

In the medical field, a medical image obtained by imaging by employing various methods such as CT and MRI is used for making a diagnosis. In a diagnosis using the medical image, in order that the diagnosis is performed while information that is not directly represented in the image is also taken into account. For example, a doctor may also appropriately check imaging information related to the medical image in addition to the medical image. U.S. Patent Application Publication 2002/0122578 proposes that a determination is made as to whether to generate character string data in accordance with an imaging condition, and the character string data is automatically arranged to eliminate the burden of manually arranging the character string data for each imaging operation.

In the diagnosis, a follow-up observation for observing the same objective over time is performed to understand the effects of surgery or medication, or the like. In the follow-up observation, due to the reason that a plurality of medical images of similar regions which are obtained from similar directions by employing similar imaging methods are used in many cases, for example, there is a particularly high need to associate information indicating the period that has elapsed between a reference time such as the date of the surgery or medication and the image and check the image in accordance with the elapsed period. However, according to the above-described technology, the information concerning the follow-up observation is not associated with the medical image.

SUMMARY

In view of the above, an information processing apparatus for medical information according to an exemplary embodiment of the present invention includes a determination unit configured to determine whether specific information is to be associated with a medical image obtained by imaging of an object based on information related to the imaging of the object, a period obtaining unit configured to obtain information indicating a period that has elapsed between a reference time concerning the specific information and a time of imaging of the medical image, and a processing unit configured to associate with the medical image the information indicating the period as the specific information in a case where the determination unit determines that the specific information is to be associated with the medical image.

Further features of the present disclosure will become apparent from the following description of exemplary embodiments with reference to the attached drawings.

BRIEF DESCRIPTION OF THE DRAWINGS

FIG. 3 is a block diagram of the control unit according to an exemplary embodiment.

FIG. 4 is a flow chart illustrating a flow from the start to the end of X-ray imaging according to an exemplary embodiment.

FIGS. 6A and 6B illustrate a patient information input screen and an imaging maneuver selection screen according to an exemplary embodiment.

FIGS. 11A and 11B illustrate a display area for annotation setting according to an exemplary embodiment.

FIG. 12 illustrates an imaging maneuver setting screen according to an exemplary embodiment.

DESCRIPTION OF THE EMBODIMENTS

Figure 1:
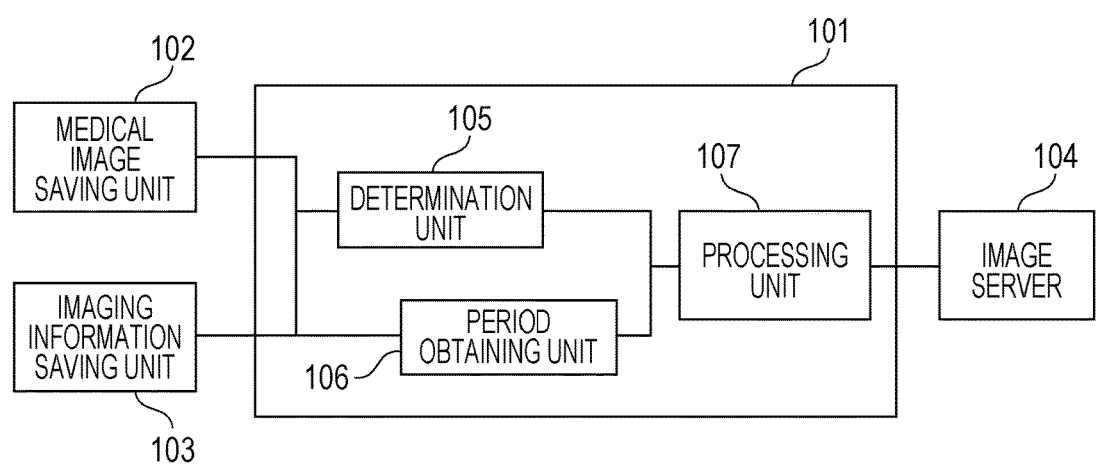
FIG. 1 illustrates a configuration of an information processing apparatus for medical information according to an exemplary embodiment.

Hereinafter, exemplary embodiments will be described by using the drawings. First, an information processing system for medical information according to an exemplary embodiment will be described on the basis of FIG. 1. The information processing system for the medical information illustrated in FIG. 1 includes an information processing apparatus 101 for medical information, a medical image saving unit 102 configured to save a medical image obtained by imaging with a medical imaging apparatus, an imaging information saving unit 103 configured to save an imaging condition of the medical image saved in the medical image saving unit 102 and the other imaging information, and an image server 104 configured to save the medical image processed by the information processing apparatus 101 for the medical information.

The information processing apparatus 101 for the medical information associates with the medical image, for example, supplementary information for the follow-up observation based on the medical image. The information processing apparatus 101 for the medical information includes a determination unit 105 configured to determine whether or not specific supplementary information is to be associated with the medical image, a period obtaining unit 106 configured to obtain information indicating the period that has elapsed between a reference time concerning the specific supplementary information and the date of imaging of the medical image when it is determined that the specific supplementary information is to be associated with the medical image, and a processing unit 107 configured to associate with the medical image the information indicating the elapsed period as the specific supplementary information. The determination by the determination unit 105 is automatically performed on the basis of information related to imaging of an object. For example, in a case where a medical image (first medical image) of the same region concerning the same object as the object in the medical image (second medical image) is saved in the medical image saving unit 102, the determination unit 105 determines that the information indicating the elapsed period concerning the medical image is to be associated on the basis of the information associated with the first medical image. In addition to this, for example, in a case where the specific supplementary information is associated with the first medical image obtained by the imaging of the same region as in the second medical image, it is determined that the information indicating the elapsed period is also to be associated with the second medical image. Alternatively, in a case where the imaging information corresponding to the medical image is imaging information for managing the elapsed period from the reference time, it is determined that the information indicating the elapsed period concerning the medical image is to be associated on the basis of the imaging information. In this manner, the determination processing by the determination unit 105 is performed on the basis of the information related to the imaging of the object. It should be noted that normal imaging information is previously specified prior to performing the imaging with an imaging apparatus (modality) for a medical image, and the medical image obtained by this imaging is associated with the imaging information after the imaging.

When it is determined that the specific supplementary information is to be associated with the medical image, the processing unit 107 associates with the medical image the information indicating the elapsed period as the specific supplementary information. According to the association herein, identification information for the medical information is included in the supplementary information including the information indicating the elapsed period, so that the information indicating the elapsed period is associated with the medical image. Alternatively, for example, an identification ID of the information indicating the elapsed period may be included in a header of the medical image, and the identification ID of the medical image may be included in the specific supplementary information to perform the association such that a mutual reference can be realized.

Accordingly, for example, when it is determined that the specific supplementary information is to be associated with the medical image, since the information indicating the period that has elapsed between the reference time and the time of the imaging can be associated with the medical image, it is possible to mitigate the burden for the user to associate the supplementary information with the medical image.

Figure 2A:
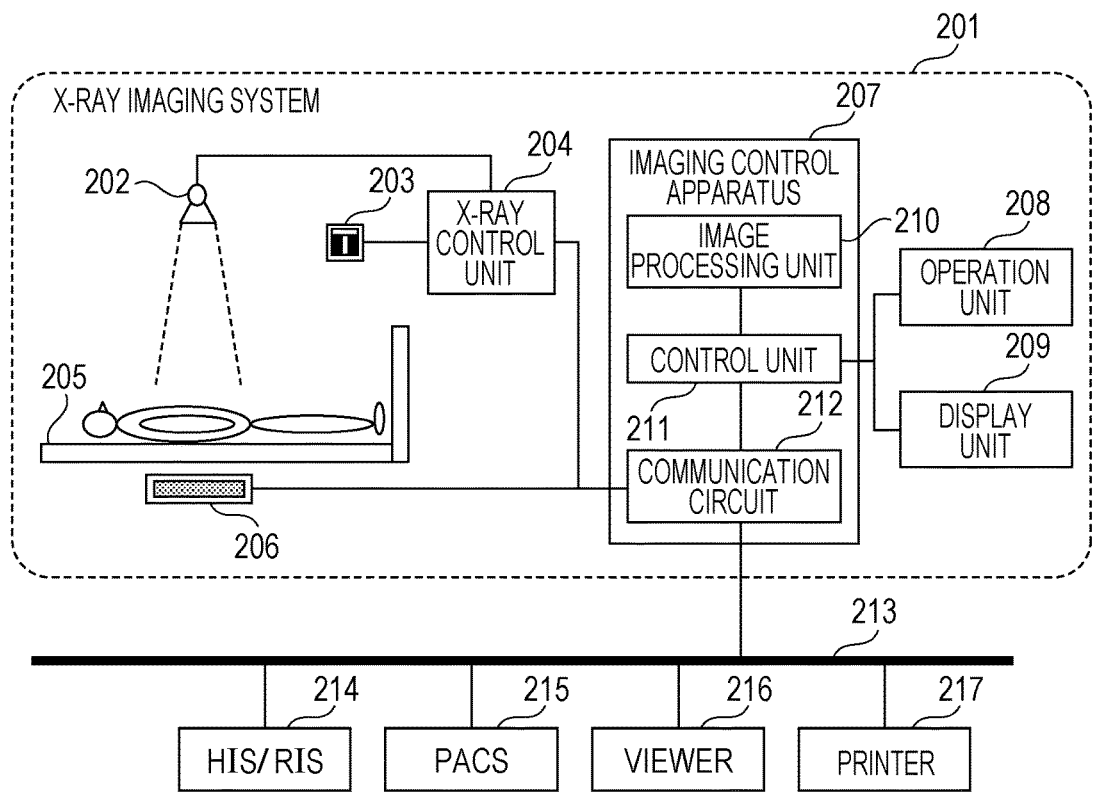
FIGS. 2A and 2B are a block diagram of an X-ray imaging system and a hardware block diagram of a control unit according to an exemplary embodiment.

FIG. 2A illustrates a configuration of an X-ray imaging system corresponding to an example of the information processing system for the medical information according to the above-described exemplary embodiment. An X-ray imaging system 201 is constituted by the X-ray generation apparatus 202, an X-ray irradiation switch 203, an X-ray control unit 204, a table 205, an X-ray sensor unit 206, an imaging control apparatus 207, an operation unit 208, and a display unit 209. It should be noted that the X-ray imaging system may be referred to as an X-ray imaging apparatus in some cases while the X-ray generation apparatus 202, the imaging control apparatus 207, and the like are regarded as units. The information processing apparatus 101 for the medical information corresponds to the imaging control apparatus 207. The medical image saving unit 102 corresponds to a memory in the X-ray sensor unit 206 or the imaging control apparatus 207. The imaging information saving unit 103 corresponds to a memory in an HIS/RIS 114 or the imaging control apparatus 207, and the image server 104 corresponds to a PACS 115. The determination unit 105, the period obtaining unit 106, and the processing unit 107 correspond to a control unit 111, for example.

The X-ray generation apparatus 202 starts and ends the X-ray radiation. The X-ray generation apparatus 202 also transmits imaging execution conditions such as an X-ray tube voltage and an X-ray tube current accompanied by the X-ray radiation to the X-ray control unit 204. The X-ray generation apparatus 202 also receives a default imaging condition from the X-ray control unit 204 and performs imaging preparation processing. The X-ray irradiation switch 203 transmits an irradiation start notification and an irradiation end notification to the X-ray control unit 204. When an operator presses a switch, the X-ray irradiation switch 203 transmits the irradiation start notification. When the operator releases the switch, the X-ray irradiation switch 203 transmits the irradiation end notification. The X-ray control unit 204 is connected to the X-ray generation apparatus 202, the X-ray irradiation switch 203, and the imaging control apparatus 207. The X-ray control unit 204 controls the X-ray radiation start and radiation end and transmits the imaging execution conditions. The X-ray control unit 204 also receives the default imaging condition from the imaging control apparatus 207 and notifies the X-ray generation apparatus 202 of the default imaging condition. The table 205 is a table on which the object is placed. The X-ray sensor unit 206 is an example of a sensor unit configured to obtain the medical image. The X-ray sensor unit 206 includes a sensor array in which a plurality of pixels are arranged in a matrix. According to an exemplary embodiment, the pixels included in this sensor array are formed of electrodes and amorphous Selenium (a-Se) that converts the X-ray into an electric signal. According to this exemplary embodiment, the a-Se and an upper electrode are arranged commonly for the plurality of pixels. A plurality of lower electrodes that collect electric charges are arranged to be apart from one another in column and row directions, and this lower electrode defines one pixel. According to another exemplary embodiment, a scintillator such as CsI:Tl that convers the X-ray into visible light is prepared. The X-ray converted into the visible light by the scintillator is converted into an electric signal by a photoelectric conversion element having sensitivity to visible light. In this case, each of the photoelectric-conversion elements defines one pixel. The above-described X-ray sensor unit 206 detects the X-rays that have been transmitted through the object to be converted into X-ray image data, so that a two-dimensional X-ray image is obtained. The X-ray sensor unit 206 is connected to the imaging control apparatus 207, and the converted X-ray image data is transmitted to the imaging control apparatus 207 together with imaging execution information such as a reading area and a binning size. The transmission of the X-ray image data and the imaging execution information is performed by way of a wired communication using a cable connected to the imaging control apparatus 207 or by way of a wireless communication. The imaging control apparatus 207 controls X-ray imaging in cooperation with the X-ray control unit 204 and the X-ray sensor unit 206, image processing such as gradation processing of the X-ray image data, execution of the examination including the X-ray imaging, input and output with respect to the operation unit 208 and the display unit 209, and transmission and reception with respect to the external apparatus via a network 213. The imaging control apparatus 207 is constituted by an image processing unit 210, a control unit 211, and a communication circuit 212. The image processing unit 210 executes image processing such as gradation processing or noise reduction processing with respect to the received X-ray image data. The control unit 211 performs a control related to the examination execution and the imaging execution or a control of the saving and reading of the execution information concerning the suspended examination and the ended examination and the X-ray image data. The communication circuit 212 transmits an X-ray irradiation preparation request and an X-ray irradiation preparation cancelling request to the X-ray control unit 204 and the X-ray sensor unit 206 via a communication I/F. The communication circuit 212 also receives the X-ray image data and the imaging information from the X-ray control unit 204 and the X-ray sensor unit 206. The communication circuit 212 also receives the examination request information, transits the examination execution information, and outputs the X-ray image data via the network 213. The operation unit 208 is an input interface configured to accept an operation by an operator. Any interface such as a keyboard, a mouse, or a multi-touch monitor may be used as the operation unit 208 functioning as the input interface as long as the operation can be input. The operation unit 208 transmits input information to the imaging control apparatus 207 in accordance with the operation. The operation unit 208 also receives the request from the imaging control apparatus 207 and performs display switching of the input interface. The display unit 209 is an output interface configured to display a user interface of control software of the X-ray imaging. Any interface such as a stand-alone monitor or a monitor built in the X-ray imaging apparatus may be used as the display unit 209 as long as the information can be displayed. A plurality of monitors that display the captured image may be connected to the single imaging control apparatus 207 in some cases, and the captured image and the past image may be subjected to a preview display on mutually different monitors in some cases. At this time, the display unit 209 determines which monitor displays which image on the basis of the notification from the imaging control apparatus 207 to perform the display. Herein, a touch panel monitor corresponding to the display unit 209 including a built-in touch panel functioning as the operation unit 208 may be used. The X-ray imaging system 201 is connected to an HIS/RIS 214, a PACS 215, a viewer 216, and a printer 217 from the imaging control apparatus 207 via the network 213. The HIS/RIS 214 is a hospital information system/radiology information system for managing information such as patient information in a radiology department and the examination request information. The PACS 215 is a server used mainly for saving images. The viewer 216 is connected to the PACS 215, and image inspection and detailed post-processing with respect to the image captured by the X-ray imaging system 201 and an examination operation are executed by using mainly a high definition monitor. The printer 217 prints out and outputs the X-ray image data.

Figure 2B:
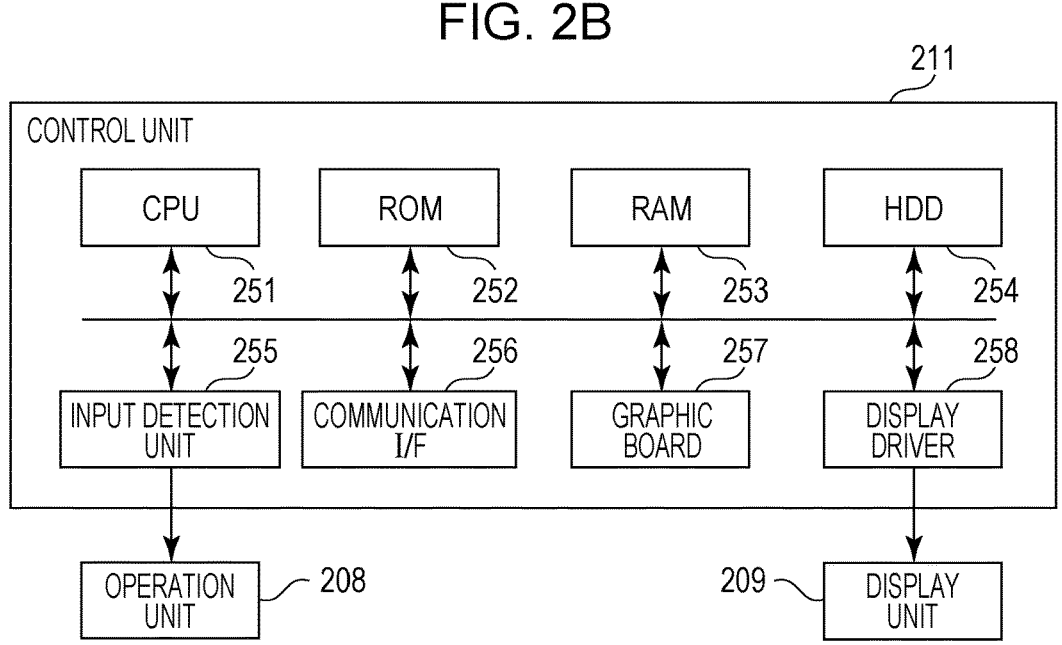

Next, FIG. 2B illustrates a hardware configuration of the control unit 211 related to the X-ray imaging system 201 according to an exemplary embodiment. The control unit 211 is constituted by a CPU 251, a ROM 252, a RAM 253, an HDD 254, an input detection unit 255, a communication I/F 256, a graphic board 257, and a display driver 258. These components are connected to one another via a bus such as a data bus. The CPU 251 is configured to control the entirety of the control unit 211 and carry out the control by executing a command program stored in the ROM 252. The CPU 251 also performs the input and output control with respect to the display unit 209 via the display driver 258 and the input and output control with respect to the operation unit 208 via the input detection unit 255. The RAM 253 is used to secure a working storage area when the CPU 251 performs the control based on the command program. The HDD 254 is an auxiliary storage apparatus configured to save various data such as the X-ray image data. The communication I/F 256 is a communication interface constituting the communication circuit 212 and performs data transmission and reception among the control unit 211, the X-ray control unit 204, the X-ray sensor unit 206, and the network 213. The graphic board 257 constitutes the image processing unit 210 and performs image processing by using a GPU.

Next, FIG. 3 illustrates a detailed configuration of the control unit 211 related to the X-ray imaging system 201 according to an exemplary embodiment. The control unit 211 is constituted by an examination information saving unit 301, an imaging maneuver information saving unit 302, an annotation information saving unit 303, a period obtaining unit 304, a determination unit 305, an imaging control unit (processing unit) 306, an examination control unit 307, an input/output control unit 308, and an image output control unit 309. Herein, the determination unit 105, the period obtaining unit 106, and the processing unit 107 in the information processing apparatus 101 for the medical information of FIG. 1 respectively correspond to the period obtaining unit 304, the determination unit 305, and the imaging control unit (processing unit) 306 in the control unit 211. The imaging information saving unit 103 corresponds to the examination information saving unit 301 and the imaging maneuver information saving unit 302. According to an exemplary embodiment, the above-described respective units indicate functions realized when the CPU 251 of FIG. 2B executes a command group included in the program expanded into the RAM 253. According to another exemplary embodiment, each of the above-described units corresponds to a hardware circuit included in a field-programmable gate array (FPGA) created for using the program.

The examination information saving unit 301 performs registration, updating, deleting, and searching of the examination information. The examination information illustrated herein includes information for identifying the examination such as patient information, examination ID, referral doctor name, diagnosing doctor name, examination description, institution name, and examination status. A follow-up observation setting for setting whether the examination is carried out for follow-up observation is also included in the examination information. The patient information illustrated herein includes all information for identifying the patient such as, patient name, patient ID, age, date of birth, sex, height, weight, and pregnancy state. The examination information saving unit 301 is constituted by a database. The imaging maneuver information saving unit 302 performs saving, updating, deleting, and searching of the imaging maneuver information. The imaging maneuver information illustrated herein includes all items that can be set for each imaging maneuver from imaging execution to post-processing and image output settings, including information for identifying the imaging maneuver such as an imaging region and an imaging direction, an imaging condition, a default value setting such as an image processing parameter, a storage transfer setting, and a print output setting. The imaging maneuver information also includes follow-up observation setting for setting whether to employ the imaging maneuver for the follow-up observation, an elapsed period character string setting, a follow-up observation situation, and a follow-up observation situation determination state. The imaging maneuver information saving unit 302 is constituted by a database. The annotation information saving unit 303 performs registration, updating, deleting, and searching of the annotation information used in the X-ray imaging system. The annotation information illustrated herein includes all items related to the arrangement of the character string data on the X-ray image, including the follow-up observation setting for setting whether the character string data and the annotation are used for the follow-up observation, a display position, a character string font, a character string font size, a default arrangement position, and the like. The annotation information saving unit 303 is constituted by a database. The period obtaining unit 304 measures an elapsed period by using an X-ray imaging image information of an arrangement objective when the follow-up observation annotation is arranged on the X-ray imaging image. The determination unit 305 determines whether the follow-up observation annotation is arranged on the X-ray imaging image by using the imaging maneuver information and the past examination information notified from the imaging control unit 306. The past examination information illustrated herein is the examination information saved in the examination information saving unit 301 after examination end processing has already been executed. The imaging control unit 306 performs data transmission and reception of, for example, a setting for whether the imaging can be performed, imaging execution conditions, and position information with respect to the X-ray generation apparatus 202 and the X-ray sensor unit 206 via the communication circuit 212. The imaging control unit 306 also controls the entire X-ray imaging flow for a single event, such as saving of the X-ray image data. The examination control unit 307 controls the overall flow of the examination execution such as updating and registration control of the patient information, planned examination information, the imaging maneuver information, and screen transition control. The input/output control unit 308 performs reception control of the input information from the operation unit 208 and display control of the display unit 209 with respect to an output instruction, such as a screen transition notified from the examination control unit 307. The image output control unit 309 determines whether the image included in the received examination information can be output and requests the communication circuit 212 to perform the image output.

Next, an example of the flow from the start to the end of the X-ray imaging examination will be illustrated by using FIG. 4 according to an exemplary embodiment. First, prior to starting the examination, in step S401, the patient information is created. The display unit 209 displays a patient information input screen 501. When a confirmation of the patient information is instructed, the operation unit 208 transmits the confirmed patient information to the examination control unit 307 via the input/output control unit 308. The examination control unit 307 newly creates the planned examination information when the patient information is received and inputs the confirmed patient information as the planned examination information. The planned examination information illustrated herein includes the patient information, the examination information, and the imaging maneuver information for where the imaging is planned for the examination. Thereafter, the examination control unit 307 obtains all of the already registered imaging maneuver information from the imaging maneuver information saving unit 302 and instructs the input/output control unit 308 to display an imaging maneuver selection screen 601 on the display unit 209. The input/output control unit 308 displays all of the received imaging maneuver information on the imaging maneuver selection screen 601 of the display unit 209.

Subsequently, in step S402, the examination information creation is performed. The examination information creation illustrated herein includes not only the input of the examination information, but also the selection of the planned imaging maneuver. When starting the examination is instructed after creating the examination information, the operation unit 208 transmits the confirmed examination information to the examination control unit 307 via the input/output control unit 308. When the examination information is received, the examination control unit 307 inputs the confirmed examination information and the imaging maneuver information as the planned examination information. It should be noted that in steps S601 and S602, the flow of manually creating the patient information, the examination information, and the planned imaging maneuver has been illustrated, but it is also possible to create the patient information, the examination information, and the planned imaging maneuver in a single event by selecting work list information obtained from the HIS/RIS 214. In this case, step S401 is omitted. When starting the examination is instructed, the operation unit 208 transmits an examination information confirmation notification including the patient information, the examination information, and the planned imaging maneuver included in the selected work list information to the input/output control unit 308. The subsequent flow is similar to the above-described content.

Subsequently, in step S403, the examination start processing is executed. The examination control unit 307 transmits the planned examination information to the examination information saving unit 301 and the input/output control unit 308 to instruct the examination start execution. The examination information saving unit 301 newly registers the received planned examination information and updates the examination status to "in progress". It should be noted that the examination status includes at least "not started yet", "in progress", "currently suspended", and "ended". When the planned examination information is received, the input/output control unit 308 displays an imaging screen 701 on the display unit 209.

Subsequently, in step S404, the selection of the imaging maneuver for executing the imaging is carried out. The selection of the imaging maneuver is made by performing a pressing operation of an imaging maneuver display section 709 displayed on the imaging screen 701. When the pressing operation of the imaging maneuver button is accepted, the operation unit 208 transmits the selected imaging maneuver information to the examination control unit 307 via the input/output control unit 308. In addition, when the selected imaging maneuver information is received, the input/output control unit 308 switches display of a sensor status display section 703 included on the imaging screen 701 of the display unit 209. When the imaging maneuver information is received, the examination control unit 307 transmits the selected imaging maneuver information to the imaging control unit 306. When the imaging maneuver information is received, the imaging control unit 306 instructs the X-ray control unit 204 and the X-ray sensor unit 206 to perform irradiation start preparation via the communication circuit 212. When the irradiation start preparation is instructed, the X-ray control unit 204 notifies the X-ray generation apparatus 202 of the default imaging condition included in the selected imaging maneuver information. Thereafter, when the condition setting of the X-ray generation apparatus 202 is completed, the X-ray control unit 204 transmits an irradiation permission notification to the communication circuit 212. When X-ray detection preparation is completed, the X-ray sensor unit 206 transmits the irradiation permission notification to the examination control unit 307 via the communication circuit 212. When the irradiation permission notification is received, the examination control unit 307 instructs the input/output control unit 308 to switch the display of the sensor status display section 703 on the imaging screen 701. In this manner, it is possible to easily determine a state in which the irradiation can be performed by switching the display of the sensor status display section 703. It should be noted that the flow of the manual selection of the imaging maneuver has been illustrated thus far, but according to aspects of the present invention, the imaging maneuver can also be automatically selected at a timing when a state in which the next imaging preparation can be performed is established such as a timing of starting the examination or a timing of the irradiation end. In this case, at the timing when the state in which the next imaging preparation can be performed is established, the examination control unit 307 obtains the imaging maneuver information in which the status is "imaging not yet performed" among the planned imaging maneuver information included in the planned examination information. The status of the imaging maneuver information includes "imaging in progress" and "imaging completed" in addition to "imaging not yet performed". The examination control unit 307 selects the imaging maneuver on the top of the registration order among the imaging maneuver information with the status of "imaging not yet performed" and transmits an irradiation permission request. It should be noted however, that the method of selecting one imaging maneuver is not limited to this. Accordingly, the burden for the operator to manually select the next imaging maneuver for each imaging operation is eliminated, and the work flow is mitigated.

Subsequently, in step S405, the X-ray imaging is executed. When the X-ray imaging is executed, the examination control unit 307 updates the status of the imaging maneuver where the irradiation is started to "imaging in progress". The examination control unit 307 also instructs the input/output control unit 308 to switch the display of the sensor status display section 703 on the imaging screen 701. The X-ray sensor unit 206 detects the emitted X-rays to be converted into the X-ray image data and transmits the X-ray image data to the X-ray control unit 204. The X-ray control unit 204 that has received the X-ray imaging image transmits the imaging execution conditions and the X-ray imaging image to the imaging control unit 306 and the examination control unit 307 via the communication circuit 212. The imaging control unit 306 executes saving of the received X-ray imaging image. The examination control unit 307 also updates the status of the imaging maneuver where the irradiation has ended to "imaging completed". Subsequently, the examination control unit 307 inputs an irradiation execution condition to the imaging maneuver information. At the same time, the examination control unit 307 instructs the input/output control unit 308 to perform the display of the sensor status display section 703 on the imaging screen 701 displayed on the display unit 209, the display of the X-ray imaging image on an image display section 702, and the updating of the corresponding display annotation on the image display section 702. It should be noted that the case where the three display controls by the input/output control unit 308 are executed at the same time has been illustrated herein, but aspects of the present invention are not limited to this. Since the imaging execution conditions may be transmitted at a timing different to that for the irradiation end notification after the irradiation end, the updating of the display annotation may be performed at a different timing.

Subsequently, in step S406, follow-up observation annotation arrangement processing is executed. This processing will be described in detail by using FIG. 5 and FIG. 8.

Subsequently, in step S407, post-processing of the X-ray image data is performed. The post-processing of the X-ray image data includes image processing such as gradation processing, geometric conversion processing such as rotation and reversal, annotation arrangement editing, cut-out area editing, and imaging failure processing. In step S406, even when it is determined that no follow-up observation annotation arrangement exists, the annotation can be manually added and arranged, and the character string of the already arranged annotation and the arrangement position can be edited in post-processing. When all the planned imaging maneuvers are completed, and the post-processing of a tomosynthesis image is completed, the end of the examination is instructed. The examination control unit 307 receives an examination end instruction notification from the operation unit 208 via the input/output control unit 308.

Subsequently, in step S408, the examination end processing is executed. The examination control unit 307 instructs the examination information saving unit 301 and the input/output control unit 308 to end the examination. At the same time, the examination control unit 307 instructs the image output control unit 309 to perform the output processing of the X-ray imaging image. The examination information saving unit 301 searches for the planned examination information from the already registered examination information in response to the examination end instruction and updates the examination status of the obtained examination information to "ended". The input/output control unit 308 shifts the screen display of the display unit 209 to the patient information input screen 501 in accordance with the examination end instruction. It should be noted that, in a case where the operation unit 208 accepts the examination suspension, the flow similar to the end of the examination also takes place. It should be however noted that, in the case of examination suspension, the examination information saving unit 301 updates the examination status of the obtained examination information to "currently suspended".

Subsequently, in step S409, the image output is executed. The image output control unit 309 performs image output processing with respect to an output apparatus 310 in response to the image output instruction via the communication circuit 212. It should be noted that the timing at which the follow-up observation annotation arrangement determination processing illustrated herein is executed is set to be after the X-ray imaging in step S406 according to the present exemplary embodiment but is not fixed to this timing. Information used for the follow-up observation annotation arrangement determination includes the patient information, the past examination information, and the imaging maneuver information. Among those, the patient information and the past examination information can be referred to at a time point when the patient information is confirmed in step S401. In addition, the imaging maneuver information is input at a time point when the examination execution information is confirmed in step S402. In view of the above, the follow-up observation annotation arrangement processing may be executed at any timing between a time point when the planned imaging maneuver information is selected in step S402 and a time point when the examination end processing is executed in step S408.

Figure 5:
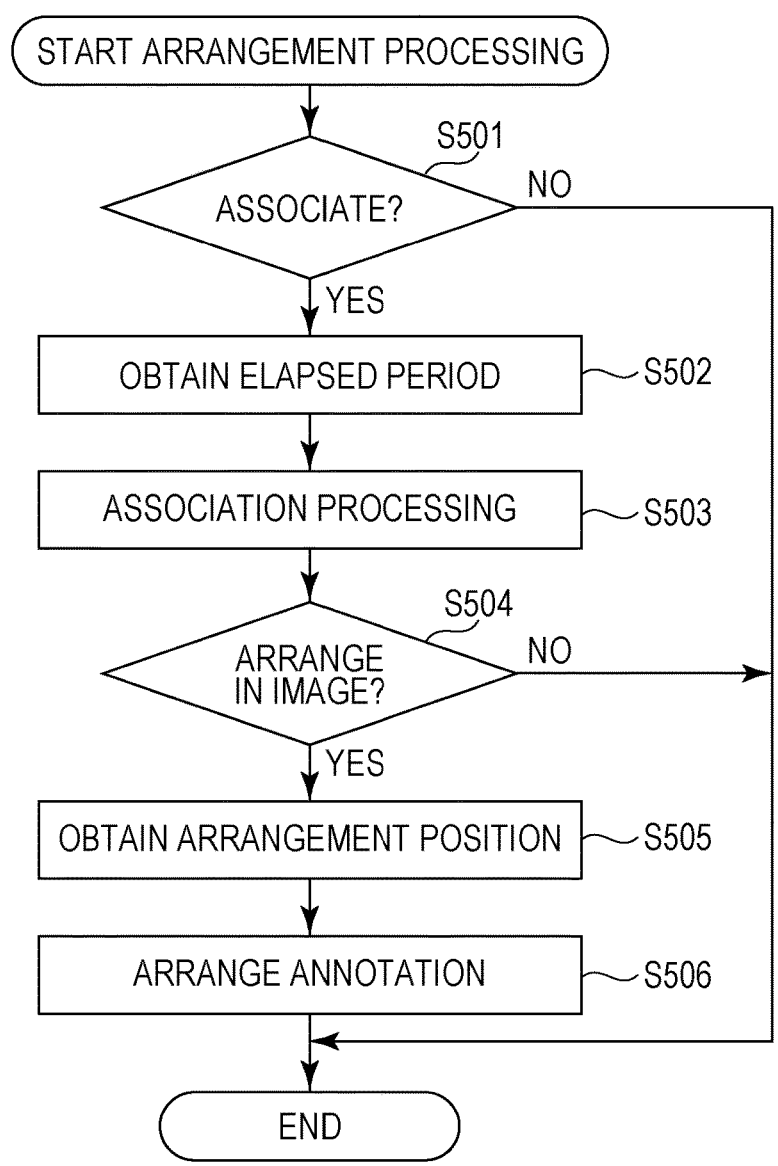
FIG. 5 is a flow chart illustrating a flow of medical information processing according to an exemplary embodiment.

A flow of the annotation arrangement processing will be described in accordance with the flow chart of FIG. 5. In step S501, the determination unit 305 determines whether specific supplementary information is associated with a medical image obtained by imaging of an object. The determination processing is performed on the basis of the information related to the imaging of the same object as in the medical image. For example, in a case where the imaging information of the medical image is imaging information for managing the elapsed period from the reference time, for example, imaging information associated with the information indicating that the imaging is for follow-up observation, it is determined that the specific supplementary information is associated with the medical image. When it is determined that the specific supplementary information is associated, the flow proceeds to step S502. It should be noted that, when it is determined that the specific supplementary information is associated, the processing is ended.

According to another exemplary embodiment, the processing is performed in the following manner in step S501. After the imaging has ended, the examination control unit 307 refers to the patient information of the patient on which the imaging has been performed and obtains the past examination information from the examination information saving unit 301. It should be noted that plural pieces of past examination information of the same patient may exist in some cases, and all past examination information is obtained by making a list of the pieces of past examination information. It should be noted that, herein, the past examination information is obtained from the examination information saved in the examination information saving unit 301, but the search objective is not limited to this. For example, a search for a server that stores the past examination information may be conducted via a network to obtain the past examination information. The examination control unit 307 transmits the past examination information and the imaging maneuver information including the captured X-ray imaging image to the determination unit 305 via the imaging control unit 306 to instruct the follow-up observation annotation arrangement determination. When the follow-up observation annotation arrangement determination instruction is received, the determination unit 305 refers to the past examination information and the imaging maneuver information including the captured X-ray imaging image to determine whether the follow-up observation annotation arrangement can be performed.

Thereafter, the determination unit 305 notifies the imaging control unit 306 of the determination as to whether the follow-up observation annotation arrangement can be performed. In a case where no follow-up observation annotation arrangement is performed, the imaging control unit 306 directly notifies the examination control unit 307 of the determination as to whether the follow-up observation annotation arrangement can be performed. After the determination of the follow-up observation annotation arrangement is received, the examination control unit 307 ends the processing.

In step S502, the period obtaining unit 304 obtains the information indicating the period that has elapsed between a reference time concerning the specific supplementary information and a time of imaging of the medical image. Herein, the reference time is, for example, a time when the processing corresponding to the objective of the follow-up observation is performed such as a time when the surgery is performed or a time when the medication is started or ended, for example. In a case where the information indicating this reference time is included in the imaging information corresponding to the medical image, this information is used. The imaging control unit 306 transmits the past examination information and the imaging maneuver information including the captured X-ray imaging image to the period obtaining unit 304 and instructs an elapsed period measurement. In a case where the information indicating this reference time is not included in the imaging information, the input/output control unit (display control unit) 308 displays a screen (GUI) for the user to input the information indicating the reference time by an operation input. In this case, the period obtaining unit 304 obtains the time input by the user as the reference time. The display timing is set in accordance with a state in which the imaging information is specified for the imaging, for example, a state in which an examination start instruction section 611 illustrated in FIG. 6B is pressed. The period obtaining unit 304 further calculates an elapsed period by obtaining a difference between the reference time and the time of the imaging of the medical image. The information associated with the medical image when the imaging of the medical image is performed may be used for the time of the imaging of the medical image. After the elapsed period is measured, the period obtaining unit 304 notifies the imaging control unit 306 of the calculated elapsed period.

According to an exemplary embodiment, in step S501, the determination unit 305 determines whether imaging information (first imaging information) used for the medical image in step S405 is imaging information for managing the elapsed period from the reference time. The determination is performed on the basis of the presence or absence of a follow-up observation ID associated with each follow-up observation. It is assumed that the imaging information is managed by an XML format, and a tag indicating the follow-up observation ID is provided to tag information of the XML. In a case where a value corresponding to this tag is null or 0, it is determined that this imaging information is not the imaging information for managing the elapsed period. In a case where the value corresponding to this tag is a number having predetermined digits, for example, "000001" or the like, it is determined that this imaging information is the imaging information for managing the elapsed period and determined that the follow-up observation ID is the value of the tag, for example, "000001". In a case where the imaging information is for managing the elapsed period from the reference time, furthermore, second imaging information having the same follow-up observation ID as this follow-up observation ID is searched for from the past examination information. Accordingly, the determination unit 305 functions as an identification unit configured to identify the second imaging information having the follow-up observation ID common to the first imaging information.

The period obtaining unit 304 obtains the reference time associated with the second imaging information as the reference time associated with this imaging information.

It should be noted that the reference time may be calculated from the obtained information without directly obtaining the reference time itself. For example, consideration will be given to a case where the period obtaining unit 304 obtains an elapsed period T2 concerning the second medical image in a situation where the second medical image is captured after the first medical image is captured with regard to the follow-up observation of the same clinical case. In this case, when the information indicating the elapsed period from the reference time is associated with the first medical image, by using information indicating an elapsed period T1 associated with the first medical image and a time $\Delta T$ between a time of the imaging of the first medical image and a time of the imaging of the second medical image, the elapsed period concerning the second medical image can be obtained as $T2=T1+\Delta T$.

In step S503, when it is determined that the specific supplementary information is to be associated with the medical image, the imaging control unit (processing unit) 306 associates with the medical image the information indicating the elapsed period as the specific supplementary information.

In step S504, the imaging control unit 306 determines whether the specific supplementary information is displayed in the image. The determination may be determined in accordance with the setting information, for example. In this case, the determination is performed by referring to setting information corresponding to a boolean-type variable representing a setting for displaying the specific supplementary information in the image as 0 and representing a setting for not displaying the specific supplementary information as 1. This setting information may be set before the imaging or before the examination or may be set by a button displayed on the imaging screen 701. When it is determined that the specific supplementary information is arranged, the flow proceeds to step S505, and when it is determined that the specific supplementary information is not arranged, the processing is ended.

In step S505, the imaging control unit 306 functions as a position obtaining unit configured to obtain a position where the annotation is to be arranged. In a case where the annotation is embedded in the image, a coordinate position in the image is specified. In a case where the annotation is not embedded in the image but is only displayed, the coordinate position on the imaging screen 701 is specified. Herein, the embedding of the annotation in the image refers to a state in which the medical image and the annotation are synthesized with each other to create a signal image and means that a part of data of the medical image is rewritten. The display without the embedding means that the rewriting of the image data is not performed, and the image and the annotation are displayed at the same time on the imaging screen 701. In either of the cases, the position of the annotation to be arranged may be a fixed coordinate position (upper left of the image). Alternatively, an irradiation field of the medical image may be recognized in the image processing unit 210, and the annotation may be arranged in an area outside the irradiation field. Alternatively, processing for extracting an object area may be performed in the image processing unit 210, and the annotation may be arranged in an area outside the object area.

The information indicating this arrangement position is also associated with the medical image and stored in a storage unit together with the information indicating the elapsed period. When the medical image is output together with the information indicating this arrangement position and the information indicating the elapsed period, it is possible to reproduce the similar annotation on the reception side.

According to another example, the coordinates of the arrangement position of the follow-up observation annotation may be determined by referring to the past examination information.

After the imaging control unit 306 receives the elapsed period, the imaging control unit 306 refers to the received elapsed period and the image information and the past examination information of the X-ray imaging image to create the follow-up observation annotation. The annotation is obtained by converting a character string representing the elapsed period into display image information and is, for example, a display image displaying a character string such as "post-operation 6 minutes". Herein, in a case where the annotation is embedded in the image to be arranged, when a pixel value of the arranged position is 0 (black) or 255 (white) or close to one of these values, a pixel value of the display image of the annotation is set to be different from the above-described pixel value. For example, when the pixel value of the arranged position is 0 (black), the character string is formed by using the pixel value of 255.

In step S506, the input/output control unit (display control unit) 308 displays the information indicating the elapsed period and the medical image on the display unit 209 at the same time. In a case where the annotation is embedded in the image to be arranged, the imaging control unit 306 performs the processing of embedding the image in the annotation, and then the input/output control unit (display control unit) 308 displays this image on the display unit 209.

The created follow-up observation annotation information is added to already-arranged annotation information included in the imaging maneuver information including the captured X-ray imaging image. It should be noted that the follow-up observation annotation information includes the elapsed period, the follow-up observation annotation, and the arrangement position. Thereafter, the imaging control unit 306 transmits the imaging maneuver information including the captured X-ray imaging image to the examination control unit 307. When the imaging maneuver information including the captured X-ray imaging image is received, the examination control unit 307 updates the imaging maneuver information included in the planned examination information.

Figure 10:
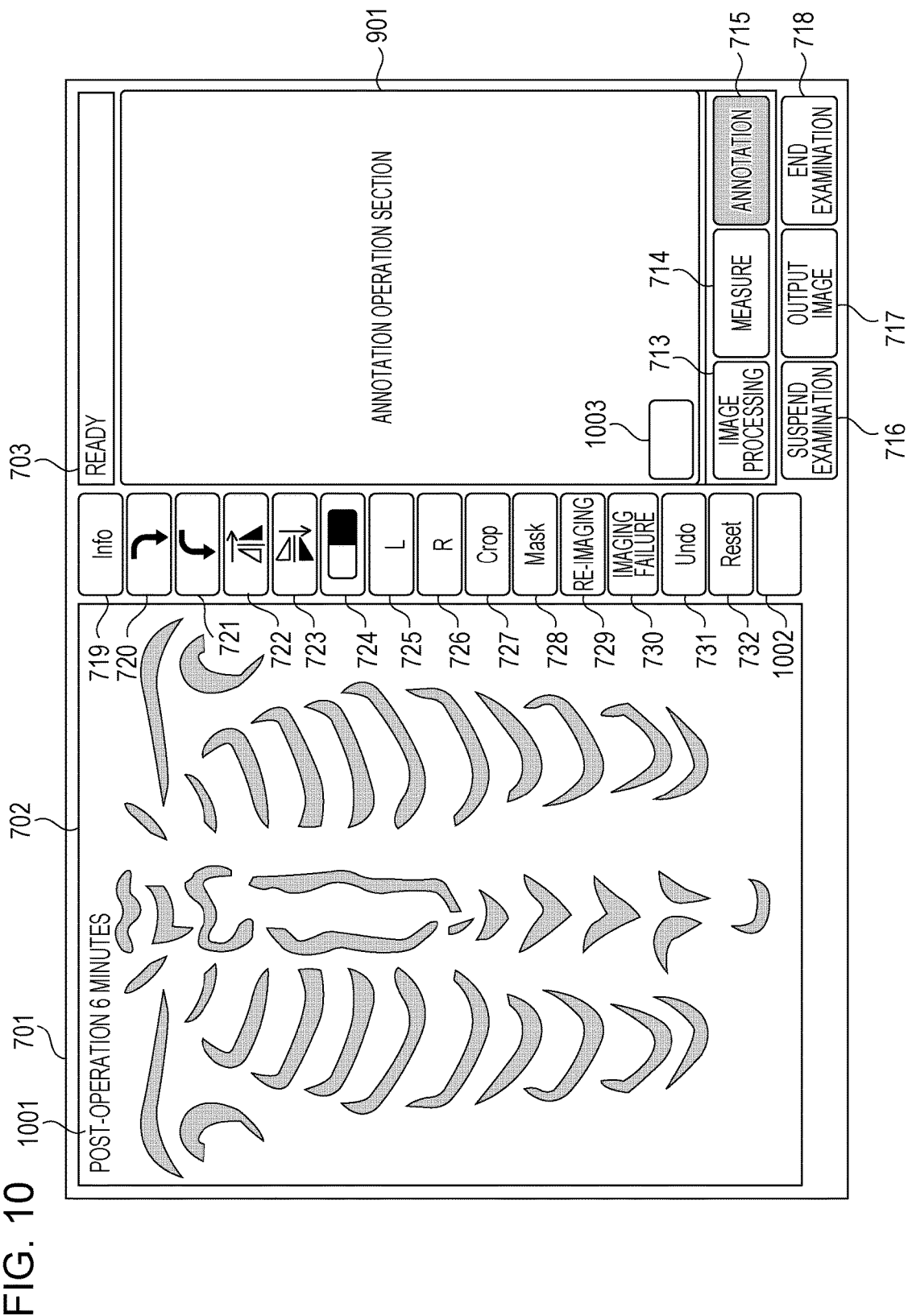
FIG. 10 illustrates an image screen immediately after follow-up observation annotation arrangement according to an exemplary embodiment.

Subsequently, the examination control unit 307 instructs the input/output control unit 308 to display the follow-up observation annotation on the image display section 702 on the imaging screen 701 by using the annotation information. When the follow-up observation annotation display instruction is obtained, the input/output control unit (display control unit) 308 refers to the arrangement position included in the annotation information and displays the specified follow-up observation annotation on the X-ray imaging image displayed on the image display section 702 on the imaging screen 701 (see the already arranged annotation 1001 of FIG. 10). In this manner, the determination as to whether the follow-up observation annotation arrangement can be performed and the character string annotation creation and arrangement are automatically executed, so that it is possible to eliminate the burden for the operator to determine the annotation arrangement each time the imaging is performed and the burden of creating and arranging the annotation. In addition, by following the format of the annotation used from the past examination information up to the previous time, it is possible to avoid such a risk that the format of the follow-up observation annotation differs while depending on the operator who performs the arrangement. Furthermore, it is possible to avoid a calculation error of the elapsed period caused by a human error by automatically calculating the elapsed period.

Hereinafter, a detail of the screen configuration will be described according to an exemplary embodiment.

Figure 6A:
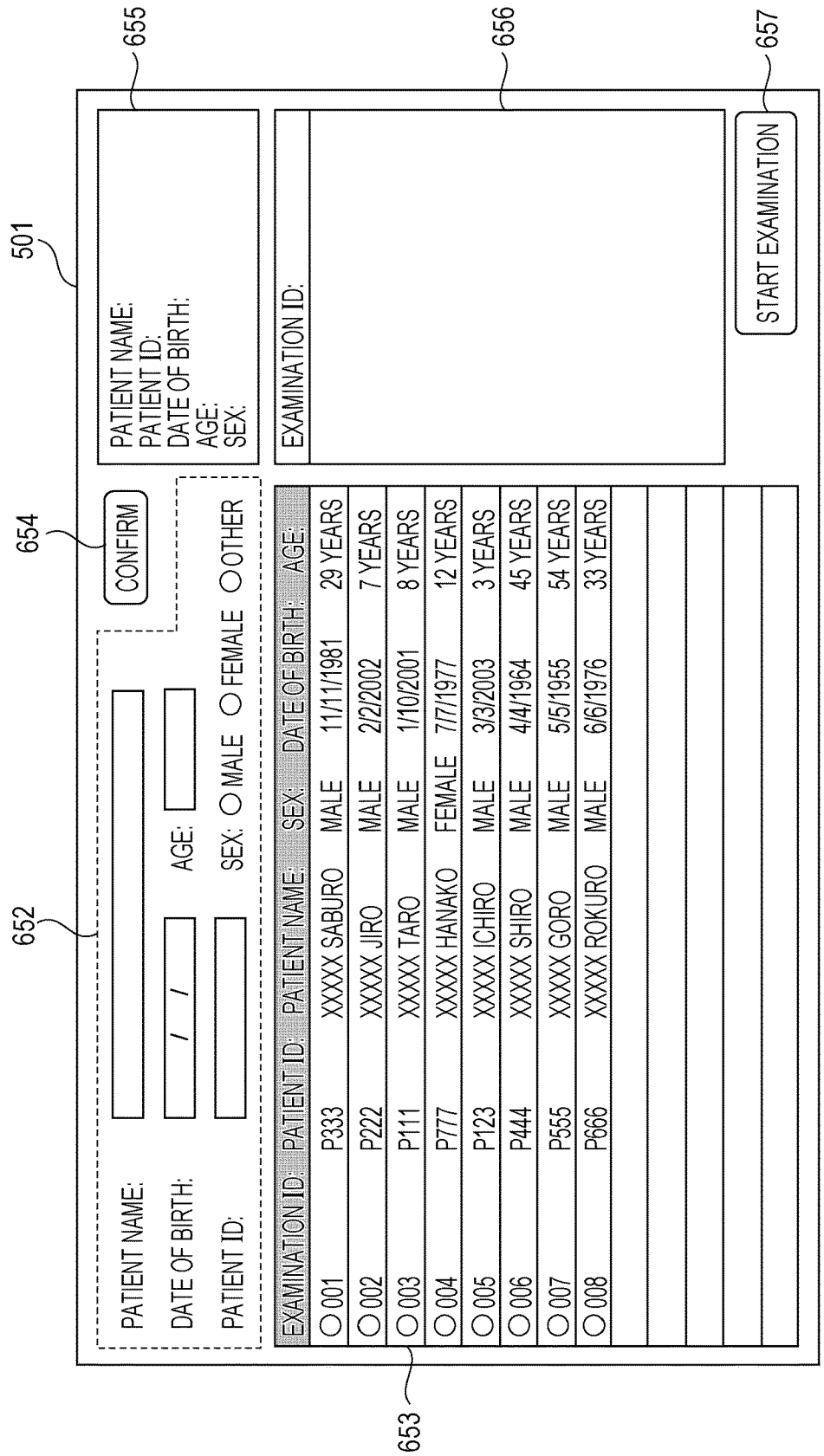

First, an example of the patient information input screen 501 displayed in step S401 in FIG. 4 will be described by using FIG. 6A. The patient information input screen 501 is a screen for inputting information of the patient corresponding to the examination execution objective. The patient information input screen 501 is constituted by a patient information input section 502, a patient information list 503, a patient information confirmation instruction section 504, a patient information display section 505, an examination information display section 506, and an examination start instruction section 507. The patient information input section 502 is a region where the input or selection of the values of the respective items included in the patient information is performed. For the patient information list 503, the patient information of the examinations executed in the past is displayed in the list. For each column, one item included in the patient information is displayed in a column of the patient information list 503. The patient information for one person is displayed in one column for the list part. When arbitrary patient information on the list is selected, the selected patient information is input to the respective input units of the patient information input section 502. The patient information confirmation instruction section 504 is a button for confirming the value input to the patient information input section 502 as the patient information. When the button is pressed, it is checked whether a value is input in a required input item and a correct value that is not against a standard is input in the input item, and when no problem occurs, the value is confirmed as the patient information. The patient information display section 505 is a region where the confirmed patient information is displayed. Until the patient information is confirmed, the values are not displayed in the respective items, and the values are displayed when the patient information is confirmed. The examination information display section 506 is a region where the input examination information is displayed. The examination information illustrated herein includes the information for identifying the examination such as the examination ID, the referral doctor name, the diagnosing doctor name, the examination description, and the institution name. In addition, the imaging maneuver selected as the planned imaging is included. It should be noted that at least one or more of the imaging maneuvers can be selected with respect to one examination. Regions where the respective items of the examination information are displayed and a region where the selected imaging maneuver is displayed exist in the examination information display section 506. Until the examination information is input, the values are not displayed in the respective items. Similarly, until the imaging maneuver is selected, the imaging maneuver is not also displayed. When the examination information is input or the imaging maneuver is selected, each item is displayed. In addition, a plurality of examinations can be executed in a single event in the single imaging. At this time, the examination information display sections 506 are lined up and displayed by the number corresponding to the number of examinations. The examination start instruction section 507 is a button for instructing to start the examination. When this button is pressed, it is checked whether the patient information and the examination information are input and also if one or more imaging maneuvers are selected for the respective examination. When no problem occurs, the examination start processing is executed. In a case where even one examination in which the imaging maneuver is not selected exists, the imaging maneuver selection screen 601 is displayed.

Next, an example of the imaging maneuver selection screen 601 displayed in step S402 in FIG. 4 will be described by using FIG. 6B. The imaging maneuver selection screen 601 is a screen for selecting the imaging maneuver for the planned imaging in the planned examination. The imaging maneuver selection screen 601 is constituted by an imaging maneuver display section 602, an imaging maneuver button 603, a patient information display section 604, examination information display sections 605 (605a, 605b), selected imaging maneuver buttons 606 (606a, 606b, 606c), an examination and imaging maneuver execution order moving-up instruction section 607, an examination and imaging maneuver execution order moving-down instruction section 608, an examination addition instruction section 609, an examination and imaging maneuver deletion instruction section 610, and the examination start instruction section 611. The imaging maneuver display section 602 is a region where the imaging maneuver buttons 603 are lined up and displayed. Each of the imaging maneuvers saved in the imaging maneuver information saving unit 302 is displayed as the imaging maneuver button 603. It should be noted that the display position of the imaging maneuver button 603 can be arbitrarily changed. In addition, in a case where the items are not fit into one page, the items can be displayed over a plurality of pages, and a displayed page is switched in response to a page switching instruction. The imaging maneuver button 603 is a button for each of the imaging maneuvers saved in the imaging maneuver information saving unit 302. At least a name of the imaging maneuver and a used sensor name are displayed on the imaging maneuver button 603. When the imaging maneuver button 603 is pressed, the selection is confirmed as the planned imaging in the selected examination. The patient information display section 604 is a region where the confirmed patient information is displayed. The examination information display section 605 is a region where the input examination information is displayed. It should be noted that a plurality of examinations can also be executed in the single imaging according to the exemplary embodiment. In a case where a plurality of examinations are executed, as indicated by the examination information display sections 605a and 605b, the items are lined up and displayed while the examination information display section 605 is distinguished. The imaging maneuver button 603 selected by the imaging maneuver display section 602 is displayed on the selected imaging maneuver button 606. One or more imaging maneuvers can be selected for the examination. In a case where a plurality of imaging maneuvers are selected, as indicated by the selected imaging maneuver buttons 606a, 606b, and 606c, each time the imaging maneuver button is selected, the selected imaging maneuver button 606 is added to the rear of the examination information display section 605. The examination and imaging maneuver execution order moving-up instruction section 607 is a button for instructing moving-up of the planned execution order of the examinations or the imaging maneuvers. The examination information display section 605 and the imaging maneuver button 606 can be selected one each on the imaging maneuver selection screen 601. When the examination and imaging maneuver execution order moving-up instruction section 607 is pressed in a state in which the examination information display section 605 is selected, the position of the currently selected examination information display section 605 is switched with its upper position of the examination information display section 605 to be moved up by one level. It should be however noted that, in a case where the leading examination information display section 605 is selected, the moving-up is not performed. In addition, when the examination and imaging maneuver execution order moving-up instruction section 607 is pressed in a state in which the imaging maneuver button 606 is selected, the position of the currently selected imaging maneuver button 606 is switched with its upper position of the imaging maneuver button 606 in the same examination to be moved up by one level. It should be however noted that, in a case where the leading imaging maneuver button 606 in the same examination is selected, the moving-up is not performed. The examination and imaging maneuver execution order moving-down instruction section 608 is a button for instructing moving-down of the planned execution order of the examinations or the imaging maneuvers. When the examination and imaging maneuver execution order moving-down instruction section 608 is pressed in a state in which the examination information display section 605 is selected, the position of the currently selected examination information display section 605 is switched with its lower position of the examination information display section 605 to be moved down by one level. It should be however noted that, in a case where the rearmost examination information display section 605 is selected, the moving-down is not performed. In addition, when the examination and imaging maneuver execution order moving-down instruction section 608 is pressed in a state in which the imaging maneuver button 606 is selected, the position of the currently selected imaging maneuver button 606 is switched with its lower position of the imaging maneuver button 606 in the same examination to be moved down by one level. It should be however noted that, in a case where the rearmost imaging maneuver button 606 in the same examination is selected, the moving-down is not performed. The examination addition instruction section 609 is a button for instructing a new addition of an examination. When the examination addition instruction section 609 is pressed, the new addition is made to the rearmost position of the examination information display section 605. The examination and imaging maneuver deletion instruction section 610 is a button for instructing deletion of the examination or the imaging maneuver. When the examination and imaging maneuver deletion instruction section 610 is pressed in a state in which the examination information display section 605 is selected, all the imaging maneuver buttons 606 included in the currently selected examination information display section 605 and the currently selected examination information display section 605 are deleted. In addition, when the examination and imaging maneuver deletion instruction section 610 is pressed in a state in which the imaging maneuver button 606 is selected, the currently selected imaging maneuver button 606 is deleted. The examination start instruction section 611 is a button for instructing to start the examination. When the examination start instruction section 611 is pressed, it is checked whether the patient information and the examination information are input and also if one or more imaging maneuvers are selected for the respective examinations, and when no problem occurs, the examination start processing is executed. When the examination start processing is executed, the screen is shifted to the imaging screen 701. In a case where even one examination in which the imaging maneuver is not elected exists, the user is notified that the imaging maneuver is to be selected, and the screen transition is not performed. The imaging maneuver selection screen 601 having the above-described configuration is displayed.

Figure 7:
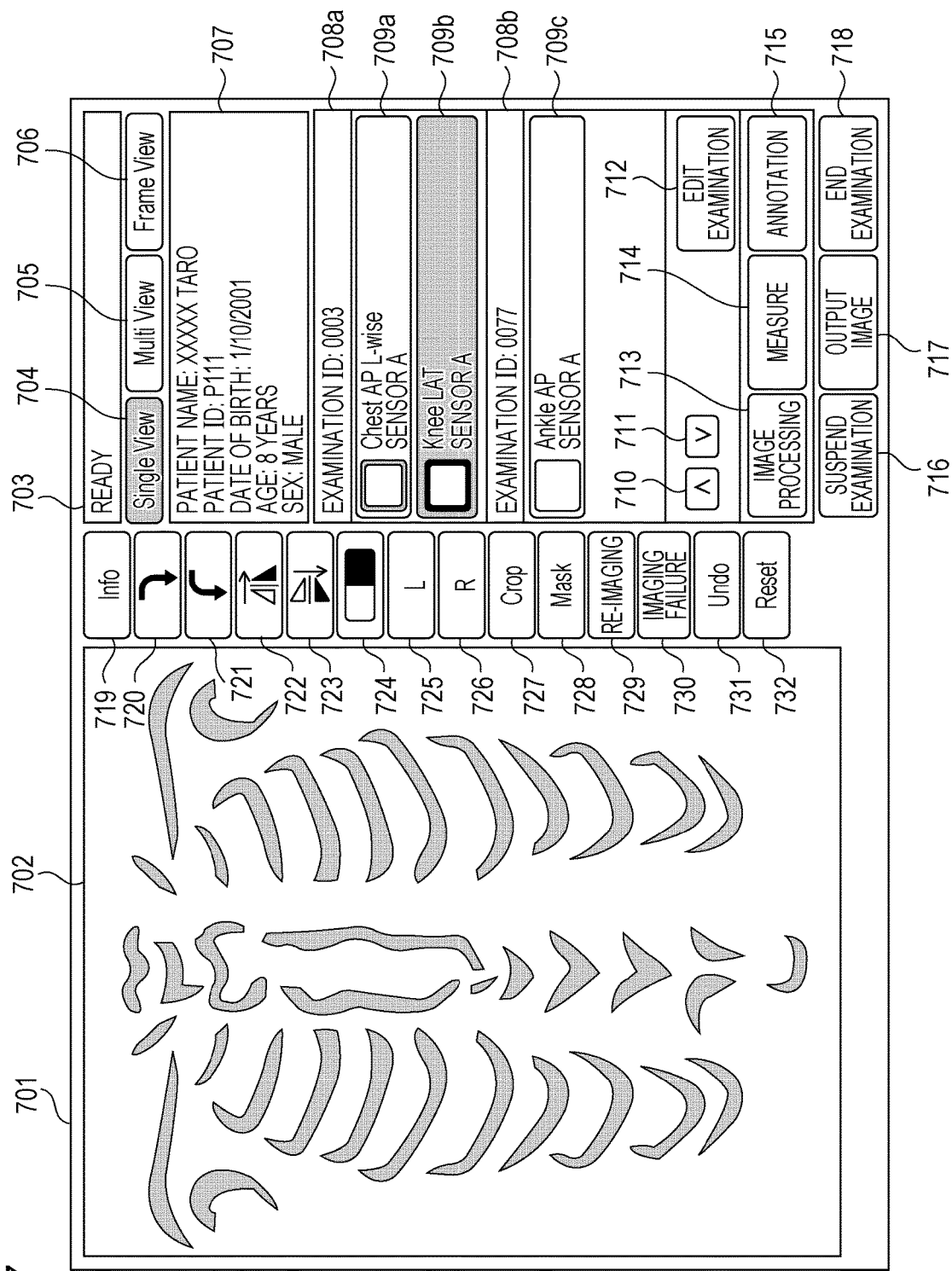
FIG. 7 illustrates an imaging screen according to an exemplary embodiment.

Next, an example of the imaging screen 701 displayed in step S403 in FIG. 4 will be illustrated by using FIG. 7. The imaging screen 701 is constituted by the image display section 702, a status display section 703, a single view instruction section 704, a multi view instruction section 705, a frame view instruction section 706, a patient information display section 707, an examination information display section 708, the imaging maneuver display section 709, an imaging maneuver execution order moving-up instruction section 710, an imaging maneuver execution order moving-down instruction section 711, an examination editing instruction section 712, an image processing instruction section 713, a measurement instruction section 714, an annotation editing instruction section 715, an examination suspension instruction section 716, an image output instruction section 717, an examination end instruction section 718, a display annotation display switching instruction section 719, a clockwise rotation instruction section 720, an anti-clockwise rotation instruction section 721, a horizontal inversion instruction section 722, a vertical inversion instruction section 723, a black-and-white inversion instruction section 724, an L-mark arrangement instruction section 725, an R-mark arrangement instruction section 726, a cut-out setting instruction section 727, a mask processing instruction section 728, a re-imaging instruction section 729, an image failure instruction section 730, an undo instruction section 731, and a reset instruction section 732. Preview display of a captured X-ray image is performed in the image display section 702. In a case where switching to the preview selection is performed after the imaging, the X-ray image selected for the preview is subjected to the preview display. In addition, the annotations of the patient information, the examination information, the irradiation condition, and the like are displayed in accordance with settings. It should be noted that the image is not displayed in an initial state immediately after the examination is started. The status display section 703 is a region where a status notified from the X-ray control unit 204 or an X-ray detector 104 is displayed while colors and characters are distinguished from one another such that the operator can easily identify the status. The imaging control unit 306 that has received the status notification from the X-ray control unit 204 or the X-ray detector 104 via the communication circuit 212 notifies the examination control unit 307 of the status change. The examination control unit 307 determines a display content on the basis of a combination of statuses of the X-ray control unit 204 and the X-ray detector 104 and transmits a status display switching instruction to the input/output control unit 308. For example, in a case where the X-ray control unit 204 does not perform the X-ray irradiation or the X-ray detector 104 does not detect the X-ray, "Not Ready" is displayed on the sensor status. On the other hand, in a case where the X-ray control unit 204 can perform the X-ray irradiation and the X-ray detector 104 can detect the X-ray, "Ready" is displayed on the sensor status, and its background color is changed to a color that is easily distinguished from the background color used when "Not Ready" is displayed. The single view instruction section 704 is a button for switching to a single view where one frame of the image selected for the preview is displayed on the image display section 702. In the case of an image having a plurality of frames, another frame can be displayed or a moving image can also be reproduced during the preview display in accordance with a keyboard or mouse operation. The multi view instruction section 705 is a button for switching to a multi view where the image display section 702 is divided into a plurality of grid-like display regions, and an image group captured during the currently executed examination is displayed side by side. This button is invalid until two or more images are captured during the currently executed examination, and the multi view display is not performed. The frame view instruction section 706 is a button for switching to a frame view where the image display section 702 is divided into a plurality of grid-like display regions, and a frame image group of the moving image selected for the preview is displayed side by side. This button is invalid in a case where the image selected for the preview is not the moving image, and the frame view display is not performed. The patient information display section 707 is a region where the patient information such as the patient name and the patient ID is displayed. The examination information such as the examination ID and the examination description are displayed on the examination information display section 708, and the imaging maneuvers selected for the examination are displayed side by side in the imaging maneuver display section 709. The imaging maneuver information such as the names of the imaging maneuvers and all of executed and captured image thumbnails 1011 are displayed on the imaging maneuver display section 709. In addition, before the imaging is performed, planned imaging thumbnails are included in the imaging maneuver display section 709, and after the imaging is performed, captured image thumbnails are included in the imaging maneuver display section 709. The imaging maneuver execution order moving-up instruction section 710 is a button for instructing moving-up of the planned execution order of the imaging maneuvers. When the imaging maneuver execution order moving-up instruction section 710 is pressed in a state in which the imaging maneuver display section 709 is selected, the position of the currently selected imaging maneuver display section 709 is switched with its upper position of the imaging maneuver display section 709 in the same examination to be moved up by one level. It should be however noted that, in a case where the leading imaging maneuver display section 709 in the same examination is selected, the moving-up is not performed. The imaging maneuver execution order moving-down instruction section 711 is a button for instructing moving-down of the planned execution order of the imaging maneuvers. When the imaging maneuver execution order moving-down instruction section 711 is pressed in a state in which the imaging maneuver display section 709 is selected, the position of the currently selected imaging maneuver display section 709 is switched with its lower position of the imaging maneuver display section 709 in the same examination to be moved down by one level. It should be however noted that, in a case where the rearmost imaging maneuver display section 709 in the same examination is selected, the moving-down is not performed. The examination editing instruction section 712 is a button for instructing the shift to the imaging maneuver selection screen 601 for examination editing. The image processing instruction section 713 is a button for instructing the switching of display and non-display of an image processing operation section. The measurement instruction section 714 is a button for instructing the switching of display and non-display of a measurement operation section. The annotation editing instruction section 715 is a button for an instructing the switching of display and non-display of an annotation operation section 901. The examination suspension instruction section 716 is a button for instructing the suspension of the currently executed examination. The image output instruction section 717 is a button for instructing the image output of the captured image included in the currently executed examination. The examination end instruction section 718 is a button for instructing the end of the currently executed examination. The display annotation display switching instruction section 719 is a button for the switching of display and non-display of the display annotation on the image display section 702. The clockwise rotation instruction section 720 is a button for rotating the captured image in the preview display in a clockwise manner. The anticlockwise rotation instruction section 721 is a button for rotating the captured image in the preview display in an anticlockwise manner. The horizontal inversion instruction section 722 is a button for horizontally inverting the captured image in the preview display. The vertical inversion instruction section 723 is a button for vertically inverting the captured image in the preview display. The black-and-white inversion instruction section 724 is a button for inverting a window value of the captured image in the preview display. The L-mark arrangement instruction section 725 is a button for arranging a laterality marker "L" on the captured image in the preview display. This button can be switched between ON and OFF, in which "L" is arranged at the time of ON, and "L" is deleted at the time of OFF. The R-mark arrangement instruction section 726 is a button for arranging a laterality marker "R" on the captured image in the preview display. This button can be switched between ON and OFF, in which "R" is arranged at the time of ON, and "R" is deleted at the time of OFF. The cut-out setting instruction section 727 is a button for instructing the setting of a cut-out of a target region with respect to the captured image in the preview display. The mask processing instruction section 728 is a button for instructing mask processing of the captured image in the preview display. The re-imaging instruction section 729 is a button for instructing re-imaging with respect to the imaging maneuver including the image currently selected for the preview. The re-imaging illustrated herein refers to processing of executing the imaging failure processing of the image where the re-imaging is instructed and newly adding the same imaging maneuver. The image failure instruction section 730 is a button for instructing image failure with respect to the image currently selected for the preview. When the imaging failure processing is executed, an image failure included in the image information is switched to ON. The undo instruction section 731 is a button for instructing undo processing of returning a processing history with respect to the image currently selected for the preview in a reverse chronologic order. The reset instruction section 732 is a button for discarding all the processing of the image currently selected for the preview and instructing resetting processing for restoring a state immediately before the imaging. The imaging screen 701 having the above-described configuration is displayed.

Figure 8:
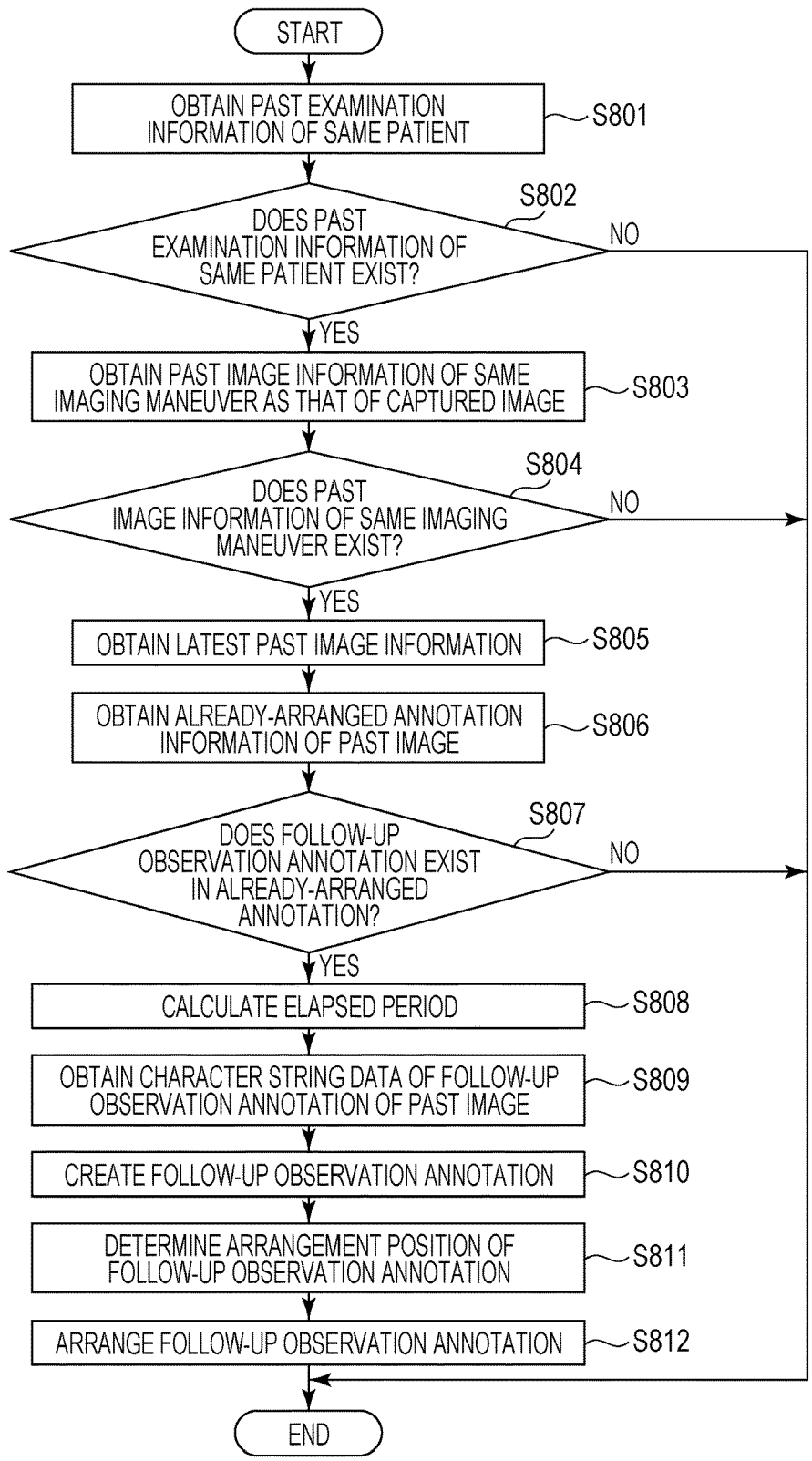
FIG. 8 is a flow chart illustrating a flow of follow-up observation annotation arrangement processing according to an exemplary embodiment.

Next, a flow of the follow-up observation annotation arrangement processing according to the exemplary embodiment will be illustrated by using FIG. 8. First, in step S801, past examination information of the patient who has been subjected to imaging of an X-ray imaging image corresponding to an arrangement objective of the follow-up observation annotation (hereinafter, will be referred to as an X-ray imaging image of the arrangement objective) is obtained. The examination control unit 307 obtains the past examination information on the basis of the patient information of the patient who has been subjected to the imaging by the examination information saving unit 301. Thereafter, the examination control unit 307 transmits the past examination information to the determination unit 305 via the imaging control unit 306 and instructs the follow-up observation annotation arrangement determination.

Subsequently, in step S802, it is checked whether the past examination information of the patient who has been subjected to the imaging exists. When the follow-up observation annotation arrangement determination instruction is received, the determination unit 305 checks the past examination information. In a case where the past examination information does not exist, it is determined that a history of an examination that has been performed on the same patient in the past does not exist, and "no follow-up observation annotation arrangement" is determined. In a case where the past examination information exists, subsequently, in step S803, the captured image and the past image information of the same imaging maneuver are obtained. The determination unit 305 obtains all the imaging maneuvers included in all of the received past examination information. Subsequently, in step S804, it is checked whether the X-ray imaging image of the arrangement objective and the same imaging maneuver exist in all the obtained imaging maneuvers. The determination unit 305 performs the checking by comparing the imaging maneuver of the X-ray imaging image of the arrangement objective with all the obtained imaging maneuvers. Any information may be used as a comparison objective as long as the information indicates the imaging region included in the imaging maneuver information. In a case where the same imaging maneuver does not exist, "no necessity of follow-up observation annotation arrangement" is determined. In a case where the X-ray imaging image of the same imaging maneuver does not exist, the determination unit 305 determines "no follow-up observation annotation arrangement". In a case where the same imaging maneuver exists, all the same imaging maneuver information is obtained. Subsequently, in step S805, the latest X-ray imaging image is obtained. The determination unit 305 obtains imaging start times included in all the obtained imaging maneuver information and obtains the imaging maneuver information in which the imaging start time is closest to that of the X-ray imaging image of the arrangement objective. It should be noted that the imaging start times are obtained for the comparison herein, but any information may be used as long as the imaging order can be determined by the information. Subsequently, in step S806, the already-arranged annotation information of the past image is obtained. The determination unit 305 obtains the already-arranged annotation information registered in the past image information included in the latest imaging maneuver information obtained in step S805. It should be noted that the already-arranged annotation information includes the annotation information arranged on the X-ray imaging image in the form of the list structure. Subsequently, in step S807, it is determined whether the follow-up observation annotation exists in the already-arranged annotation information. The determination unit 305 obtains all the annotation information included in the already-arranged annotation information and checks whether the follow-up observation annotation in which the setting of the follow-up observation is ON exists. In a case where the follow-up observation annotation does not exist, the determination unit 305 determines "no necessity of follow-up observation annotation arrangement". On the other hand, in a case where the follow-up observation annotation exists, the determination unit 305 determines "follow-up observation annotation arrangement is necessary". After the determination unit 305 determines whether the follow-up observation annotation arrangement can be performed, the follow-up observation annotation arrangement determination result is transmitted to the imaging control unit 306. After the follow-up observation annotation arrangement determination result is received, in the case of "no necessity of follow-up observation annotation arrangement", the imaging control unit 306 directly notifies the examination control unit 307 of the follow-up observation annotation arrangement determination result and ends the follow-up observation annotation arrangement processing. On the other hand, in the case of "follow-up observation annotation arrangement is to be performed", the flow is shifted to the creation of the follow-up observation annotation. With the above-described method, a case having a markedly high probability that the follow-up observation annotation is to be arranged is detected, and whether the arrangement is to be performed can be automatically determined. In the case of "follow-up observation annotation arrangement is to be performed", subsequently, in step S808, an elapsed period is calculated. The imaging control unit 306 transmits the X-ray imaging image information of the arrangement objective and the latest past image information to the period obtaining unit 304 and instructs the elapsed period measurement. When the elapsed period measurement instruction is received, the period obtaining unit 304 first determines an elapsed period measurement objective time. The imaging start time of the latest past image obtained in step S805 is used as the elapsed period measurement objective time, for example. It should be however noted that the information is not limited to this as long as the time when the imaging is executed can be understood by using the information. In addition, the elapsed period input to the follow-up observation annotation arranged in the latest past image may be used. It should be noted that, in a case where a plurality of follow-up observation annotations are arranged in the latest past image, one of the follow-up observation annotations is selected. Subsequently, the period that has elapsed between the elapsed period measurement objective time and the imaging start time of the X-ray imaging image of the arrangement objective is calculated. After the elapsed period measurement, the period obtaining unit 304 notifies the imaging control unit 306 of the elapsed period measurement result. Subsequently, in step S809, the character string data of the follow-up observation annotation included in the latest past image is obtained. When the elapsed period measurement result is received, the imaging control unit 306 obtains the character string data of the follow-up observation annotation included in the latest past image. It should be noted that, in a case where a plurality of follow-up observation annotation are arranged in the latest past image, the character string data of one of the follow-up observation annotations is selected. Subsequently, in step S810, the creation of the follow-up observation annotation is performed. The imaging control unit 306 creates a new follow-up observation annotation by combining the obtained character string data with the elapsed period. Accordingly, in a case where the follow-up observation with respect to the same patient continues, since the same character string data is regularly arranged in a state in which only the elapsed period is updated, it is possible to smoothly execute the diagnostic reading. Subsequently, in step S811, the arrangement position of the newly created follow-up observation annotation is determined. The imaging control unit 306 inputs the arrangement position of the follow-up observation annotation included in the latest past image to the arrangement position of the newly created follow-up observation annotation. Accordingly, in a case where the follow-up observation with respect to the same patient continues, since the follow-up observation annotation is regularly arranged at the same position, it is possible to smoothly execute the diagnostic reading. Subsequently, in step S812, the arrangement of the follow-up observation annotation is performed. The imaging control unit 306 transmits the follow-up observation annotation information including the follow-up observation annotation arrangement determination result, the follow-up observation annotation, the follow-up observation annotation, the arrangement position, and the like to the examination control unit 307. When the follow-up observation annotation information is received, the examination control unit 307 refers to the follow-up observation annotation arrangement determination result. In the case of "follow-up observation annotation is to be arranged", the content of the follow-up observation annotation information is added to the annotation arrangement information of the X-ray imaging image information of the arrangement objective included in the planned examination information. Thereafter, the input/output control unit 308 is instructed to display the character string data specified on the X-ray imaging image in the image display section 702 on the imaging screen 701 displayed on the display unit 209 (see the already arranged annotation 1001 in FIG. 10).

Figure 9A:
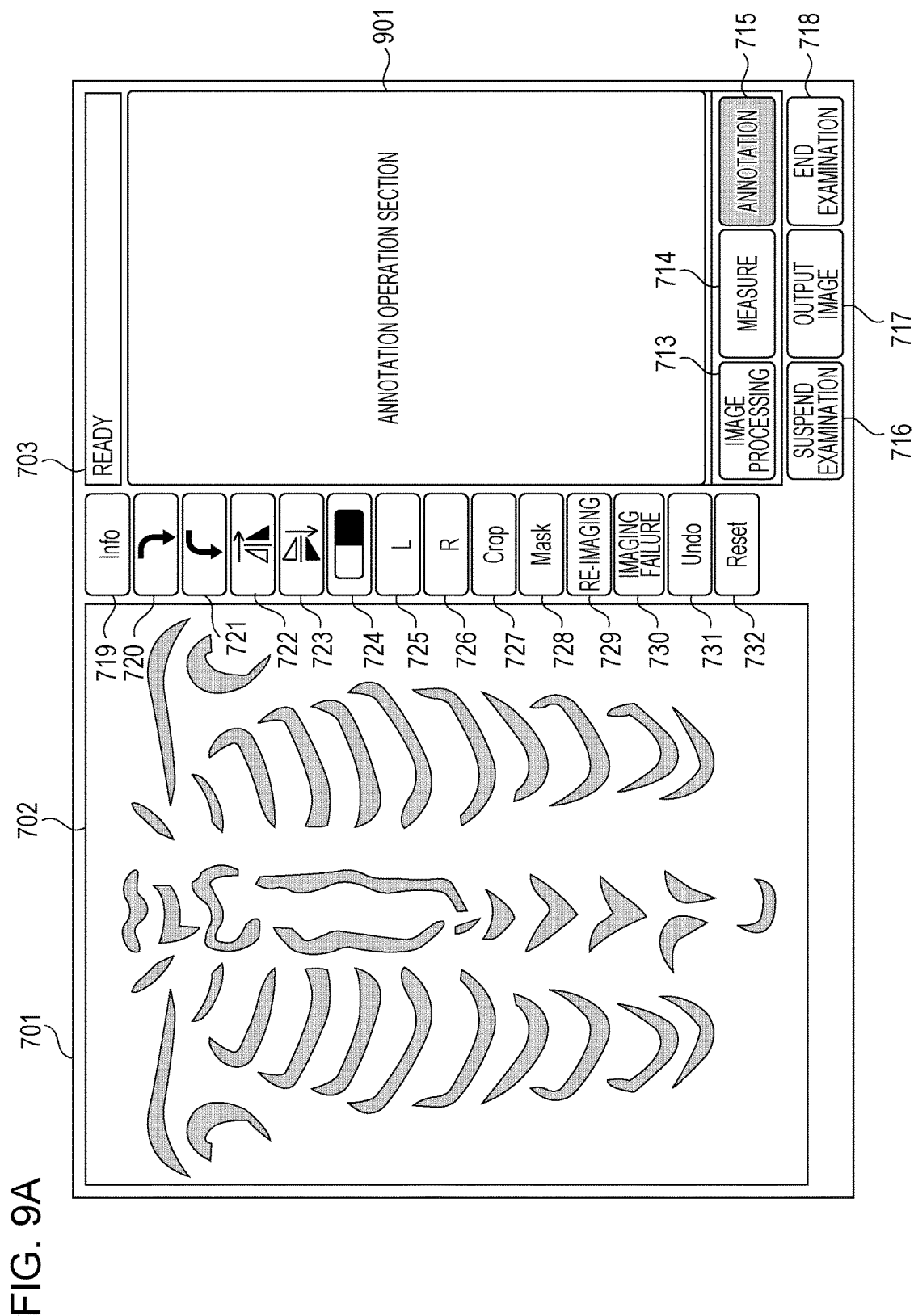
FIGS. 9A and 9B illustrate an annotation operation unit according to an exemplary embodiment.
Figure 9B:
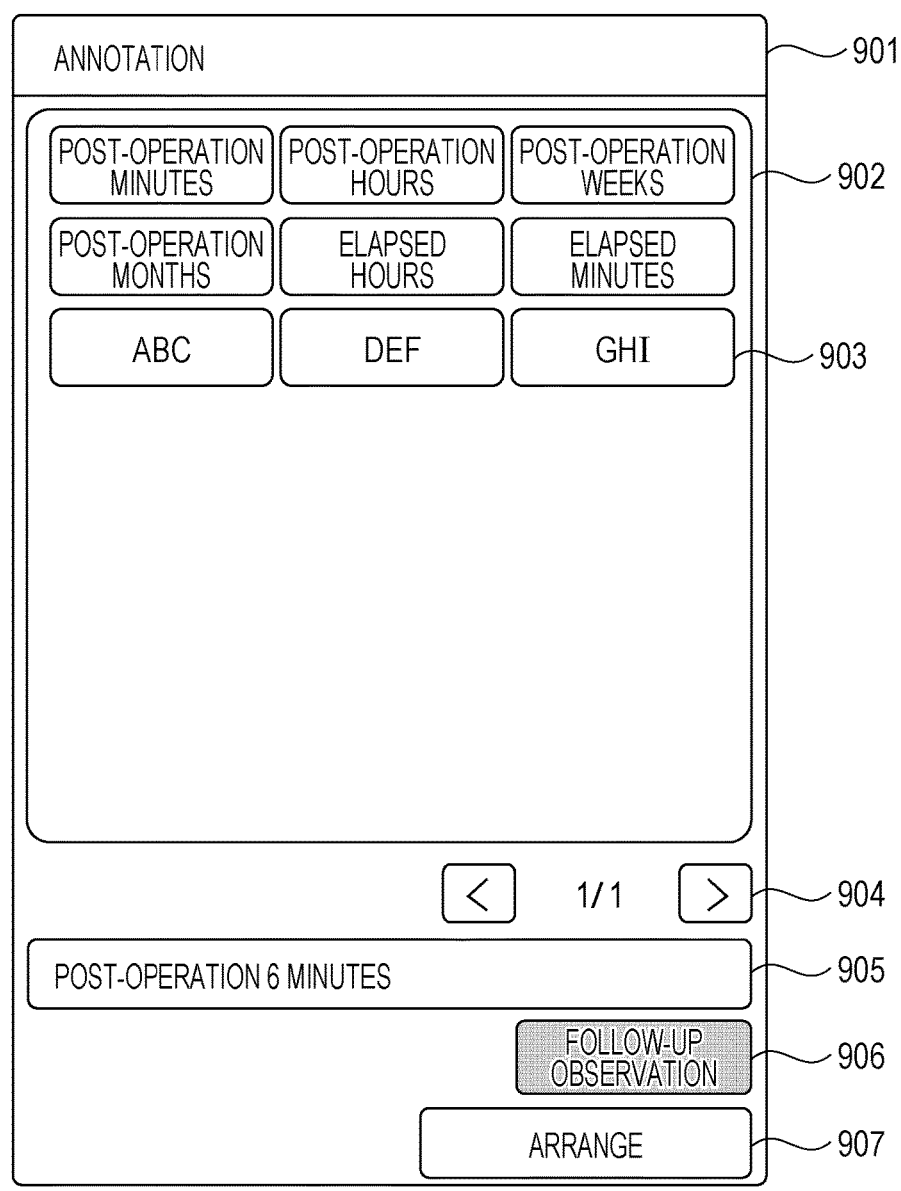

Next, an example of the annotation operation section 901 will be illustrated by using FIGS. 9A and 9B. When the annotation editing instruction section 715 is switched to ON, the annotation operation section 901 is displayed on the imaging screen 701 as illustrated in FIG. 9A. When the annotation editing instruction section 715 is switched to OFF, the annotation operation section 901 is put into a non-display state. As illustrated in FIG. 9B, the annotation operation section 901 is constituted by a registered character string annotation display section 902, a registered character string annotation button 903, a registered character string annotation display switching instruction section 904, a character string annotation editing section 905, a follow-up observation instruction section 906, and an annotation arrangement instruction section 907. The registered character string annotation display section 902 is a region where pieces of the character string annotation information saved in the annotation information saving unit 303 are displayed side by side. The respective pieces of the character string annotation information are displayed in the registered character string annotation display section 902 side by side in accordance with an array system set in the annotation setting. In a case where the number of registrations of the registered character string annotation information are not fit into the registered character string annotation display section 902, the registered character string annotation display section 902 is divided into a plurality of pages. When the annotation editing instruction section 715 is switched to ON, the operation unit 208 transmits an annotation display request notification to the input/output control unit 308. When the annotation display request notification is received, the input/output control unit 308 transmits the annotation display request notification to the examination control unit 307. When the annotation display request notification is received, the examination control unit 307 transmits a registered annotation obtaining request notification to the annotation information saving unit 303. When the registered annotation obtaining request notification is received, the annotation information saving unit 303 obtains all the saved character string annotations and transmits the registered annotation information to the examination control unit 307.

It should be noted that the registered annotation information includes the annotation character string and the information whether the follow-up observation can be performed. When the registered annotation information is received, the examination control unit 307 transmits the registered annotation information to the input/output control unit 308. When the registered annotation information is received, the input/output control unit 308 creates the annotation operation section 901 on the basis of the registered annotation to be displayed on the imaging screen 701 of the display unit 209. The registered character string annotation button 903 is a button displayed for each character string annotation saved in the annotation information saving unit 303. The registered character string is displayed on the button. When the registered character string annotation button 903 is pressed, the registered character string is displayed on the character string annotation editing section 905. A setting state of the follow-up observation is set in the follow-up observation instruction section 906. The registered character string annotation display switching instruction section 904 is a button for instructing the switching of the displayed page in a case where the registered character string annotation display section 902 is divided into a plurality of pages. The character string annotation editing section 905 is a text box where the character string displayed as the annotation can be edited. For example, after the registered character string annotation button 903 in which the follow-up observation setting is ON is selected, the follow-up observation annotation character string can be manually created by inputting the elapsed period in the character string annotation editing section 905. The follow-up observation instruction section 906 is a toggle button for instructing the ON/OFF switching of the follow-up observation setting with respect to the character string annotation. The follow-up observation setting is applied to the character string input in the character string annotation editing section 905. With this configuration, the follow-up observation setting can be made to not only the already registered annotation but also the temporarily created character string. The annotation arrangement instruction section 907 is a button for instructing the arrangement of the character string input in the character string annotation editing section 905 on the image as the annotation. When the annotation arrangement instruction section 907 is pressed, the operation unit 208 transmits an annotation arrangement notification to the input/output control unit 308. It should be noted that the annotation arrangement notification includes the image information of the arrangement objective, the annotation character string, the follow-up observation setting, and the arrangement position. When the annotation arrangement notification is received, the input/output control unit 308 transmits the annotation arrangement notification to the examination control unit 307. When the annotation arrangement notification is received, the examination control unit 307 searches for the same image information as the image information included in the annotation arrangement notification from the planned examination information. After the same image information is obtained, the examination control unit 307 adds the annotation included in the annotation arrangement notification to the annotation information included in the image information. Thereafter, the examination control unit 307 inputs the arrangement position of the annotation set in the imaging maneuver of the image information to which the annotation is added, to an annotation addition notification. Thereafter, the examination control unit 307 transmits the annotation addition notification to the input/output control unit 308. When the annotation addition notification is received, the input/output control unit 308 obtains the image information currently displayed by the display unit 209. In a case where the currently displayed image information is different from the image information included in the annotation addition notification, it is determined that it is not necessary to add the annotation to be displayed, and the processing is ended. In a case where the currently displayed image information is the same as the image information included in the annotation addition notification, the character string data specified on the X-ray image displayed on the image display section 702 on the imaging screen 701 is displayed by referring to the arrangement position (see the already arranged annotation 1001 of FIG. 10). The annotation operation section 901 having the above-described configuration is displayed.

According to another exemplary embodiment, the input/output control unit 308 displays the plurality of medical images corresponding to the plural pieces of the imaging information having the common follow-up observation ID on the display unit in accordance with the operation input. The display control is performed, for example, by selecting a follow-up display button 1002 for instructing the display in accordance with the operation input to the operation unit 208. The plurality of medical images are arranged in the image display section 702. Accordingly, the follow-up observation can be more easily performed.

According to another exemplary embodiment, a temporal subtraction image is generated while the same region, the same direction, and the same range are taken into account in the follow-up observations. In a case where the second imaging information having the follow-up observation ID common to the follow-up observation ID included in the first imaging information associated with the medical image exists, the image processing unit 210 generates a subtraction image of the first medical image corresponding to the first imaging information and the second medical image corresponding to the second imaging information. It is possible to employ various related-art methods concerning temporal subtraction processing for the generation of the subtraction image. The input/output control unit 308 displays this subtraction image on the image display section 702. The generation of the subtraction image is performed in accordance with the imaging of the first medical image and the reception of the medical image by the imaging control apparatus 207 by taking into account this time-consuming processing including positioning processing and the like. When the input/output control unit 308 is set to be displayed in accordance with pressing operation of a button 1003, the user does not need to wait for a time used for the temporal subtraction processing, and it is possible to promptly display the input/output control unit 308 in accordance with the user operation. When this temporal subtraction processing is set to be started at a timing when the gradation processing or the like concerning the first medical image is ended, the display delay of the first medical image does not occur. It should be noted that the image processing unit 210 may start the image processing unit 210 in accordance with the pressing operation of the button 1003.

Next, an example of a display area 1101 for annotation setting where an operation input for setting a display format of the annotation related to the elapsed period is accepted will be illustrated by using FIGS. 11A and 11B. The examination control unit 307 functions as a setting unit configured to set the display format of the elapsed period in accordance with the operation input to the display area 1101 for annotation setting. Information indicating this set display format is associated with the medical image as the specific supplementary information together with the information indicating the period by the imaging control unit (processing unit) 306. The association processing is performed while identification information of one information is included in the other information similarly as in the above-described processing. The display area 1101 for annotation setting is, for example, a window area for previously registering a candidate of the character string annotation to be arranged on the X-ray image. The display area 1101 for annotation setting is constituted by a font setting section 1102, an array system setting section 1103, a registered annotation display section 1104, an annotation addition instruction section 1105, an annotation editing instruction section 1106, a registered annotation deletion instruction section 1107, an annotation display order moving-up instruction section 1108, an annotation display order moving-down instruction section 1109, an annotation editing cancel instruction section 1110, an annotation editing confirmation instruction section 1111, an annotation input window 1112, an annotation character string editing section 1113, a follow-up observation setting section 1114, an annotation input cancel section 1115, and an annotation input confirmation instruction section 1116. The font setting section 1102 is a region where a character string font and a font size are set which are employed when the annotation character string is arranged on the X-ray image. The array system setting section 1103 is a region for setting the number of arrays used when the registered character string annotation button 903 is displayed on the registered character string annotation display section 902 of the annotation operation section 901. Herein, a size of the registered character string annotation button 903 at the time of the display of the annotation operation section 901 is determined in accordance with the set array system. The registered annotation display section 1104 is a region where pieces of the registered annotation information are displayed in the list. For each registered annotation information, at least the annotation character string and the ON/OFF state of the follow-up observation setting are displayed. The annotation addition instruction section 1105 is a button for instructing new addition of the annotation information. When the annotation addition instruction section 1105 is pressed, the annotation input window 1112 illustrated in FIG. 11B is displayed. The annotation editing instruction section 1106 is a button for instructing editing of the registered annotation information. When the annotation editing instruction section 1106 is pressed in a state in which any of the registered annotation information on the registered annotation display section 1104 is selected, the annotation input window 1112 is displayed. The registered annotation deletion instruction section 1107 is a button for instructing deletion of the registered annotation information. When the registered annotation deletion instruction section 1107 is pressed in a state in which any of the registered annotation information on the registered annotation display section 1104 is selected, the selected registered annotation information is deleted from the annotation information saving unit 303. The annotation display order moving-up instruction section 1108 is a button for instructing moving-up of the display order of the registered annotation information. When the annotation display order moving-up instruction section 1108 is pressed in a state in which any of registered annotation information on the registered annotation display section 1104 is selected, the position of the currently selected registered annotation information is switched with its upper position of the registered annotation information, and the order is moved up by one level. It should be however noted that, in a case where the leading registered annotation information is selected, the moving-up is not performed. The annotation display order moving-down instruction section 1109 is a button for instructing moving-down of the display order of the registered annotation information. When the annotation display order moving-down instruction section 1109 is pressed in a state in which any of registered annotation information on the registered annotation display section 1104 is selected, the position of the currently selected registered annotation information is switched with its lower position of the registered annotation information, and the order is moved down by one level. It should be however noted that, in a case where the rearmost registered annotation information is selected, the moving-down is not performed. The annotation editing cancel instruction section 1110 is a button for instructing discarding of the edited content on the display area 1101 for annotation setting. The annotation editing confirmation instruction section 1111 is a button for instructing confirmation of the edited content on the display area 1101 for annotation setting to save the edited content in the annotation information saving unit 303. The annotation input window 1112 is a window where new registration and editing of the annotation character string are performed. The annotation character string editing section 1113 is a text box where input of the annotation character string is performed. The follow-up observation setting section 1114 is a toggle button where ON/OFF of the follow-up observation setting with respect to the annotation character string can be switched. The annotation input cancel section 1115 is a button for instructing discarding of the editing content on the annotation input window 1112. The annotation input confirmation instruction section 1116 is a button for instructing confirmation of the edited content on the annotation input window 1112. When the annotation input confirmation instruction section 1116 is pressed, at the time of the new addition, the registered annotation is added to the registered annotation display section 1104. At the time of the editing, the display content of the objective registered annotation is updated to the information after the confirmation. The display area 1101 for annotation setting having the above-described configuration is displayed. In this manner, while the annotation information can be registered in advance, it is possible to eliminate the burden of constantly editing and arranging the annotation character string at the time of the examination execution.

Next, an example of an imaging maneuver information setting screen 1201 will be illustrated by using FIG. 12. The imaging maneuver information setting screen 1201 is a screen where a condition and a processing content related to the imaging are collectively set as the imaging maneuver information in advance. The imaging maneuver information setting screen 1201 is constituted by a protocol name setting section 1202, a series description setting section 1203, a comment setting section 1204, a laterality marker setting section 1205, a DICOM attribute setting section 1206, an annotation setting section 1207, an imaging maneuver information setting cancel instruction section 1208, and an imaging maneuver information setting confirmation instruction section 1209. The protocol name setting section 1202 is a region where a name of the imaging maneuver is set. The series description setting section 1203 is a region where a series description is set for each of the imaging maneuvers. The comment setting section 1204 is a region where an arbitrary character string is set as a comment for the imaging maneuver. The laterality marker setting section 1205 is a region where an arrangement of the laterality marker is individually set with respect to the imaging maneuver. For each maker, at least a setting of a position for arranging the marker by default and an ON/OFF setting as to whether to automatically arrange the laterality marker immediately after the imaging are included in the laterality marker setting section 1205. Other settings related to the laterality marker may also be included in addition to the above. The DICOM attribute setting section 1206 is a region where a DICOM attribute determined by a hierarchy of the imaging maneuver is set. At least an examination region, a patient method, a position of field of view, and a setting of the laterality are included in the DICOM attribute setting section 1206. Other settings related to the DICOM attribute included in the hierarchy of the imaging maneuver may also be included in addition to the above. The annotation setting section 1207 is a region where a setting concerning the annotation character string arrangement for each of the imaging maneuvers is made. At least, a follow-up observation setting, a default character string at the time of the elapsed period character string arrangement, and a setting of the default arrangement position at the time of the annotation character string are included in the annotation setting section 1207. Other settings related to the annotation may also be included in addition to the above. In this manner, since the follow-up observation setting can be made for each of the imaging maneuvers, it is possible to automatically determine whether the follow-up observation annotation arrangement can be performed at the time of the imaging. In addition, since the default character string at the time of the follow-up observation can be set, it is possible to unify the format of the follow-up observation annotation for each of the imaging maneuvers without depending on the determination by the operator. The imaging maneuver information setting cancel instruction section 1208 is a button for instructing discarding the edited content in the imaging maneuver information setting screen 1201. The imaging maneuver information setting confirmation instruction section 1209 is a button for instructing confirmation of the edited content on the imaging maneuver information setting screen 1201. The imaging maneuver information setting screen 1201 having the above-described configuration is displayed.

Figure 13:
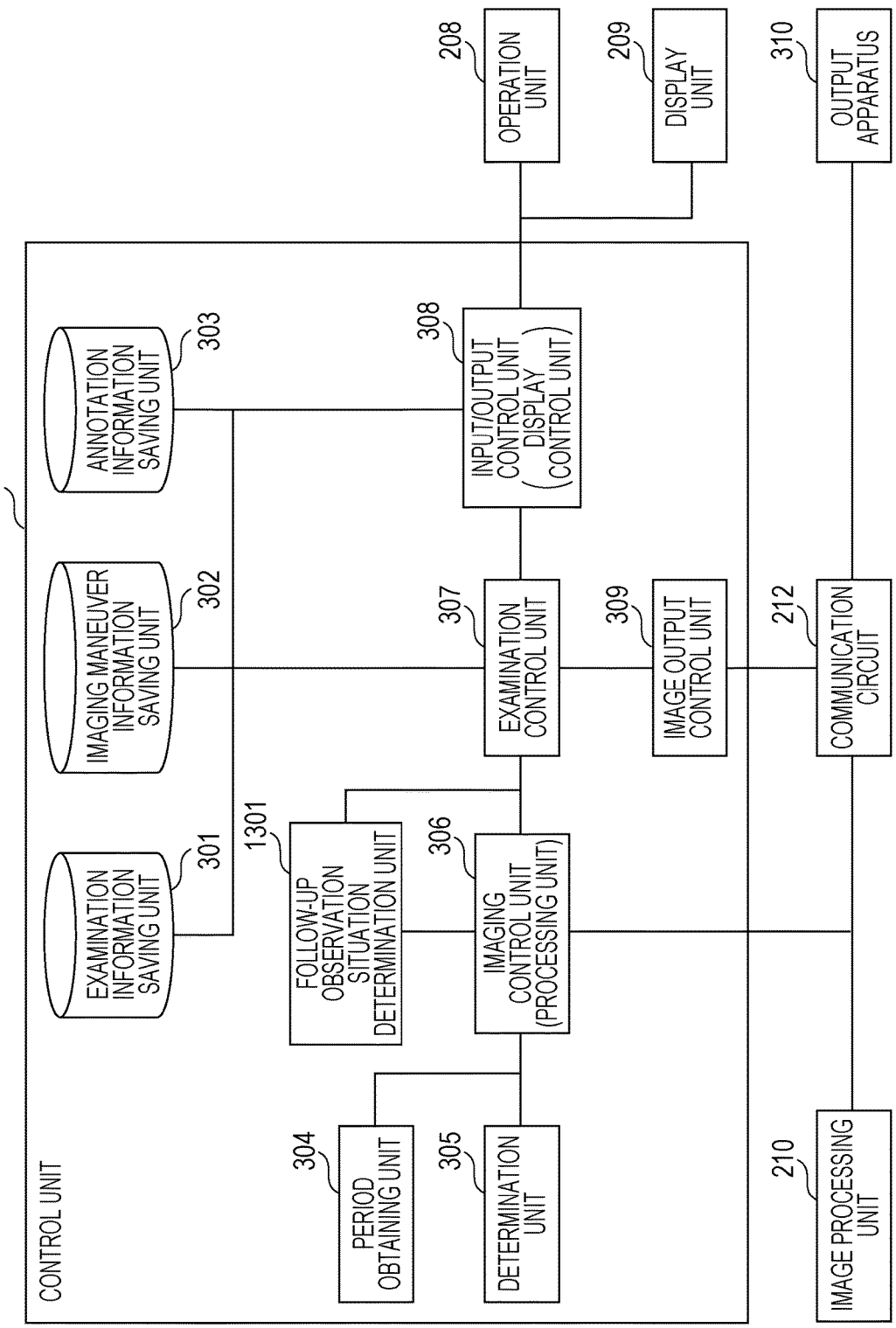
FIG. 13 is a block diagram of the control unit according to an exemplary embodiment.

Hereinafter, a configuration and an operation of the X-ray imaging system according to another exemplary embodiment will be described by using the drawings. The configuration of the X-ray imaging system and the hardware configuration of the control unit are similar to the above-described exemplary embodiment illustrated in FIG. 1, FIG. 3, and the like. FIG. 13 illustrates a detailed configuration of the control unit 211 related to the X-ray imaging system 201 according to the present exemplary embodiment. The configurations of the examination information saving unit 301 to the image output control unit 309 are similar to the configurations illustrated in FIG. 3. A follow-up observation situation determination unit 1301 uses the imaging maneuver information notified from the imaging control unit 306 or the examination control unit 307 to determine the follow-up observation situation for each imaging maneuver. It should be noted that the follow-up observation situation includes at least "follow-up observation in progress" and "no follow-up observation".

Figure 14:
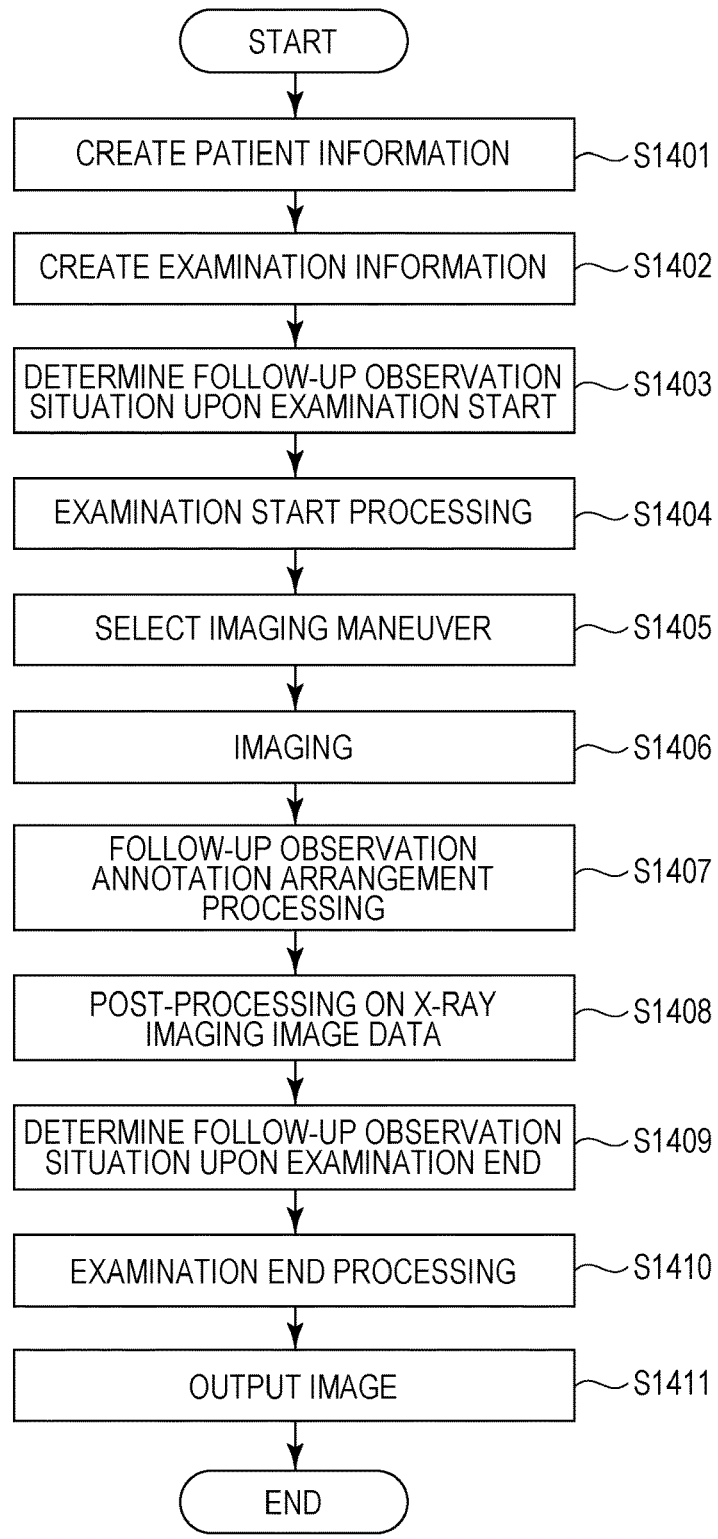
FIG. 14 is a flow chart illustrating a flow from the start to the end of X-ray imaging according to an exemplary embodiment.

Next, an example of a flow from the start to the end of the X-ray imaging examination according to the present exemplary embodiment will be illustrated by using FIG. 14. Step S1401 and step S1402 are similar to step S401 and step S402 illustrated in FIG. 4. Subsequently, in step S1403, the follow-up observation determination processing at the time of starting the examination is executed. The examination control unit 307 transmits the planned examination information to the follow-up observation situation determination unit 1301 and instructs the follow-up observation situation determination. When the follow-up observation situation determination instruction is received, the follow-up observation situation determination unit 1301 determines the follow-up observation situation with respect to all the imaging maneuver information included in the planned examination information and sets "follow-up observation in progress" or "no follow-up observation" (see FIG. 17 for details). After the follow-up observation situation determination is ended, the follow-up observation situation determination unit 1301 transmits the planned examination information to the examination control unit 307. Accordingly, at the time point when the imaging maneuver planned to be executed is confirmed before the examination is started, the setting of the follow-up observation situation can be updated, and it is possible to automatically determine the arrangement of the follow-up observation annotation with a satisfactory accuracy at the time of the imaging. The subsequent steps S1404 to S1408 are similar to steps S403 to S407 illustrated in FIG. 4. Subsequently, in step S1409, follow-up observation situation determination processing at the time of ending the examination is executed. The examination control unit 307 transmits the planned examination information to the follow-up observation situation determination unit 1301 to instruct the follow-up observation situation determination. When the follow-up observation situation determination instruction is received, the follow-up observation situation determination unit 1301 determines the follow-up observation situation with respect to all the imaging maneuver information included in the planned examination information and sets "follow-up observation in progress" or "no follow-up observation" (see FIG. 19 for details). After the follow-up observation situation determination is ended, the follow-up observation situation determination unit 1301 transmits the planned examination information to the examination control unit 307. Accordingly, the setting of the follow-up observation situation can be updated by using the state in which the imaging is completed at the time of ending the examination. The subsequent steps S1410 and S1411 are similar to steps S408 and step S409 illustrated in FIG. 4.

Hereinafter, a detail of the screen configuration according to the present exemplary embodiment will be illustrated.

Figure 15:
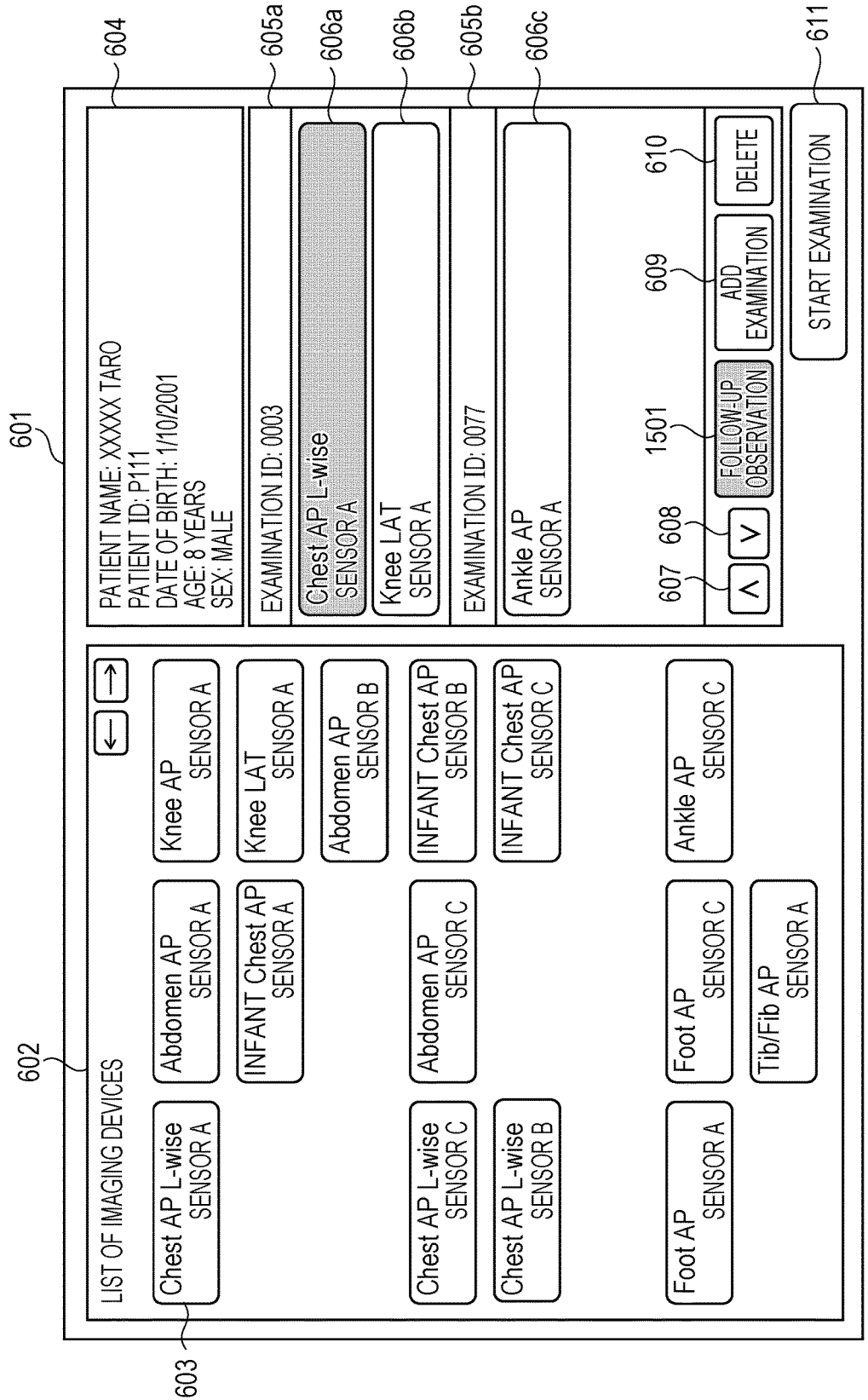
FIG. 15 illustrates the imaging maneuver selection screen according to an exemplary embodiment.

Next, an example of the imaging maneuver selection screen 601 displayed according to the present exemplary embodiment will be illustrated by using FIG. 15. According to the present exemplary embodiment, a follow-up observation situation switching section 1501 is also added to be displayed. The follow-up observation situation switching section 1501 is a toggle button for instructing switching of the start and the end of the follow-up observation with respect to the planned examination or imaging maneuver. It should be noted that the button is put into an ON state in a case where the follow-up observation situation is "follow-up observation in progress" or the follow-up observation start instruction is issued. The button is put into an OFF state in a case where the follow-up observation situation is "no follow-up observation" or the follow-up observation end instruction is issued. When the examination information display section 605 or the imaging maneuver button 606 is selected, the follow-up observation situation of the selected examination information display section 605 or the selected imaging maneuver button 606 is reflected in the follow-up observation instruction section. When the follow-up observation situation switching section 1501 is pressed in a state in which the imaging maneuver button 606 is selected, the follow-up observation situation of the selected imaging maneuver is switched. When the follow-up observation situation switching section 1501 is pressed in a state in which the examination information display section 605 is selected, the follow-up observation situations of all the imaging maneuvers included in the selected examination information display section 605 are switched. The imaging maneuver selection screen 601 having the above-described configuration is displayed.

Figure 16:
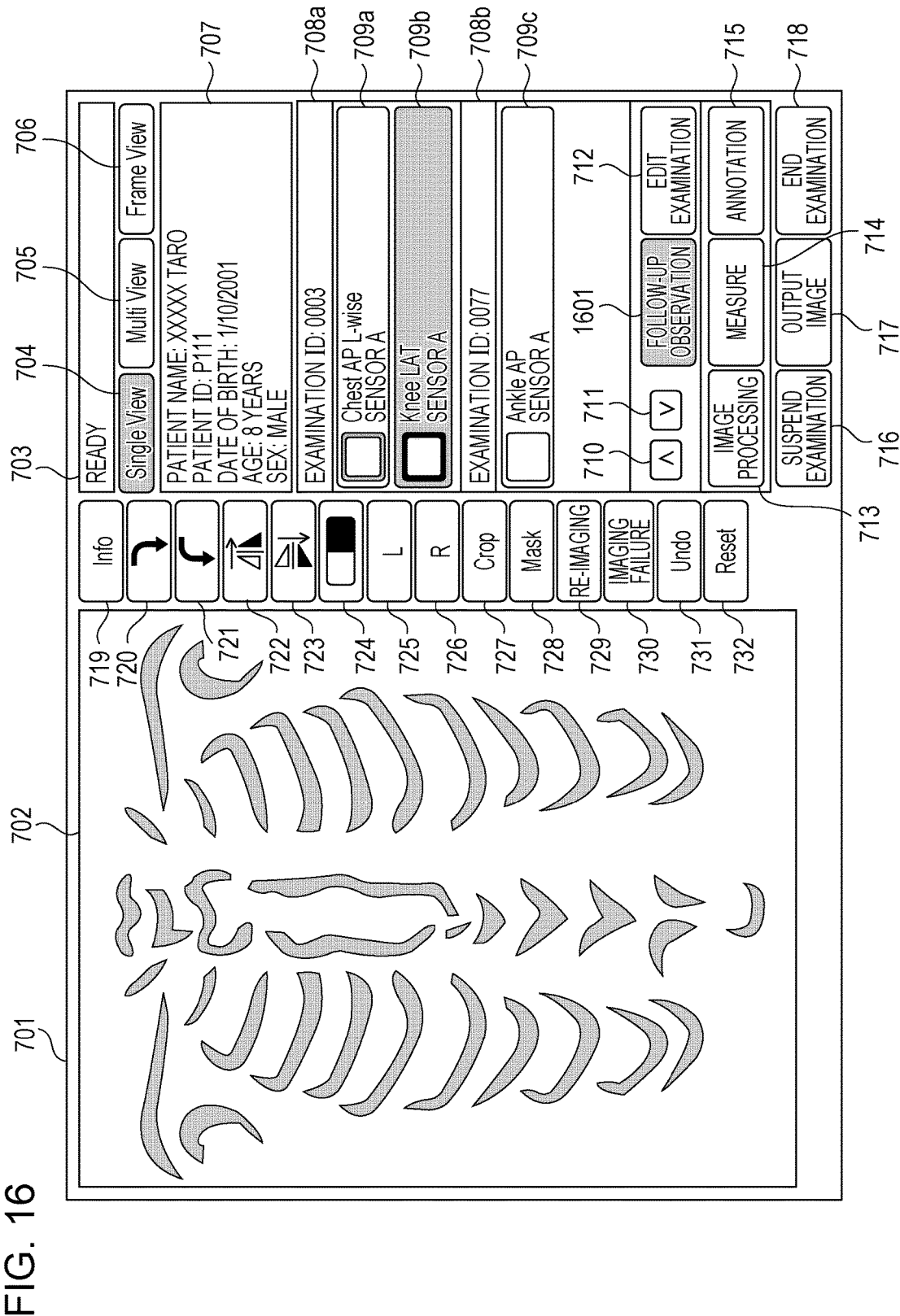
FIG. 16 illustrates the imaging screen according to an exemplary embodiment.

Next, an example of the imaging screen 701 displayed according to the present exemplary embodiment will be illustrated by using FIG. 16. According to the present exemplary embodiment, a follow-up observation situation switching section 1601 is added to be displayed. The follow-up observation situation switching section 1601 is a toggle button for instructing switching of the start and the end of the follow-up observation with respect to the currently executed examination or the imaging maneuver. It should be noted that, in a case where the follow-up observation situation is "follow-up observation in progress" or the follow-up observation start instruction is issued, the button is put into an ON state. In a case where the follow-up observation situation is "no follow-up observation" or the follow-up observation end instruction is issued, the button is put into an OFF state. In a case where the follow-up observation situation is "no follow-up observation", the button is put into the OFF state. When the examination information display section 708 or the imaging maneuver button 603 is selected, the follow-up observation situation of the selected examination information display section 708 or the selected imaging maneuver button 603 is reflected in the follow-up observation instruction section. When the follow-up observation situation switching section 1601 is pressed in a state in which the imaging maneuver button 603 is selected, the follow-up observation situation of the selected imaging maneuver is switched. When the follow-up observation situation switching section 1601 is pressed in a state in which the examination information display section 708 is selected, the follow-up observation situations of all the imaging maneuvers included in the selected examination information display section 708 are switched. The imaging screen 701 having the above-described configuration is displayed. In this manner, with the provision of the follow-up observation instruction section, the operator can change the start and the end of the follow-up observation situation any time at a determined timing while the examination is executed on the imaging screen from a time point when the imaging maneuver is selected at the time of the examination information creation.

Figure 17:
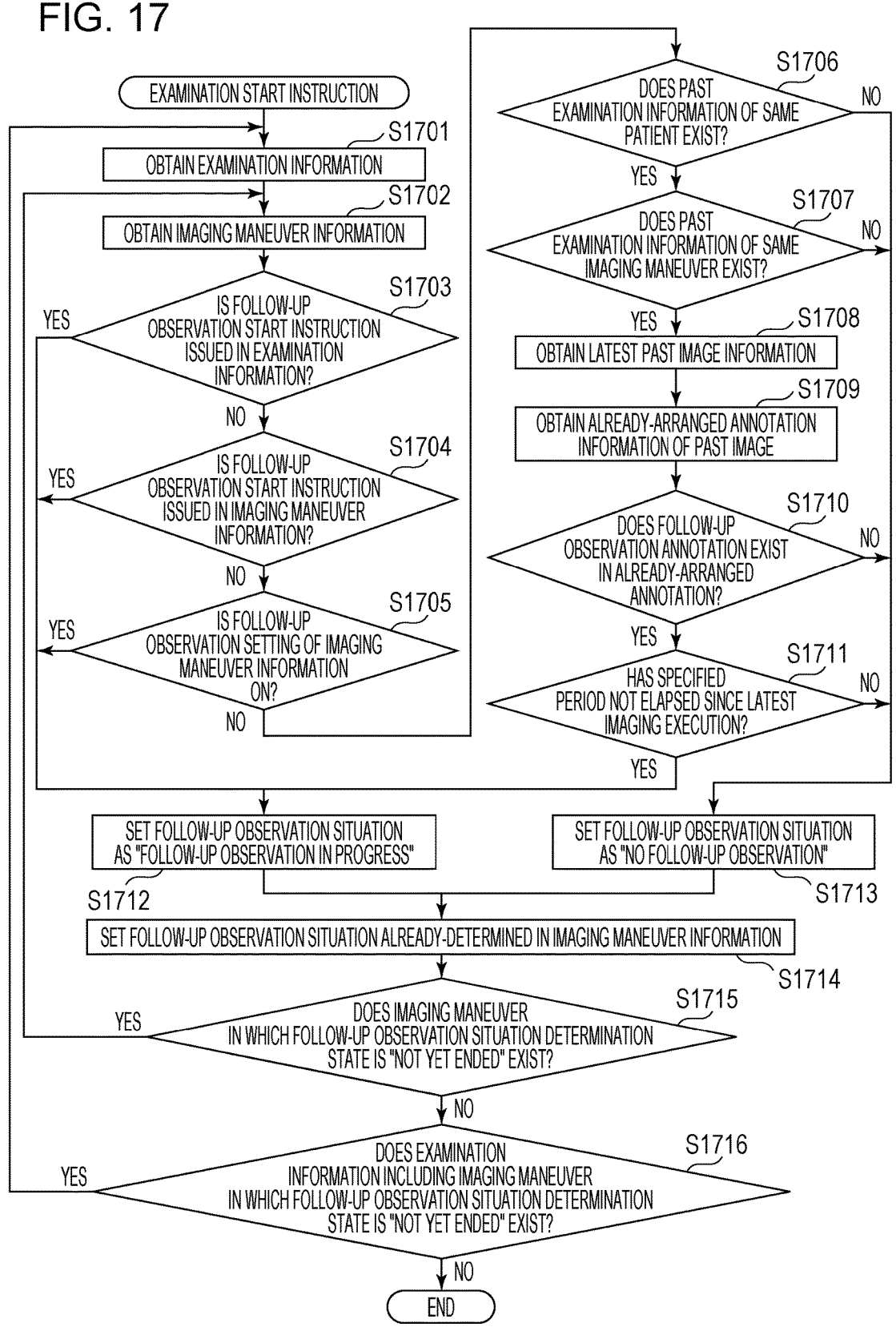
FIG. 17 is a flow chart illustrating a flow of follow-up observation situation determination processing at the time of the start of an examination according to an exemplary embodiment.

Next, a flow of the follow-up observation situation determination processing at the time of the start of the examination executed in step S1403 in FIG. 14 will be illustrated by using FIG. 17. First, in step S1701, the planned examination information is obtained. When the examination start instruction is issued, the examination control unit 307 transmits the planned examination information to the follow-up observation situation determination unit 1301 and instructs the follow-up observation situation determination. When the follow-up observation situation determination instruction is received, the follow-up observation situation determination unit 1301 obtains the planned examination information. In a case where plural pieces of the planned examination information exist, each planned examination information is sequentially obtained one by one as the determination objective examination information. Subsequently, in step S1702, the imaging maneuver information included in the planned examination information is obtained. The follow-up observation situation determination unit 1301 sequentially obtains the obtained imaging maneuver information included in the planned examination information one by one as determination objective imaging maneuver information. Subsequently, in step S1703, it is checked whether the follow-up observation start instruction is issued in the determination objective examination information. The follow-up observation situation determination unit 1301 checks the follow-up observation situation of the determination objective examination information. In a case where the follow-up observation start instruction is issued in the determination objective examination information, the follow-up observation situation of the determination objective imaging maneuver information is determined as "follow-up observation in progress". In a case where the follow-up observation start instruction is not issued in the determination objective examination information, subsequently, in step S1704, it is checked whether the follow-up observation start instruction is issued in the determination objective imaging maneuver information. The follow-up observation situation determination unit 1301 checks the follow-up observation situation of the determination objective imaging maneuver information. In a case where the follow-up observation start instruction is issued in the determination objective imaging maneuver information, the follow-up observation situation of the determination objective imaging maneuver information is determined as "follow-up observation in progress". In a case where the follow-up observation start instruction is not issued in the determination objective imaging maneuver information, subsequently, in step S1705, the follow-up observation setting of the determination objective imaging maneuver information is checked. The follow-up observation situation determination unit 1301 checks the follow-up observation setting of the determination objective imaging maneuver information. In a case where the setting is ON, the follow-up observation situation of the determination objective imaging maneuver information is determined as "follow-up observation in progress". In a case where the setting is OFF, subsequently, in step S1706, the follow-up observation setting of the determination objective imaging maneuver information is checked. The follow-up observation situation determination unit 1301 transmits a past examination information obtaining request to the examination control unit 307 via the imaging control unit 306. The examination control unit 307 obtains the past examination information of the same patient as the patient who has requested from the examination information saving unit 301 and transmits the past examination information to the follow-up observation situation determination unit 1301. The follow-up observation situation determination unit 1301 checks the received past examination information. In a case where the past examination information does not exist, the follow-up observation situation of the determination objective imaging maneuver information is determined as "no follow-up observation". In a case where the past examination information exists, subsequently, in step S1707, it is checked whether the determination objective imaging maneuver information and the same imaging maneuver exist in the past examination information. Any information may be used as the comparison objective as long as the information indicates the imaging region included in the imaging maneuver information. In a case where the same imaging maneuver does not exist, the follow-up observation situation determination unit 1301 determines the follow-up observation situation of the determination objective imaging maneuver information as "no follow-up observation". In a case where the same imaging maneuver exists, all pieces of the same imaging maneuver information are obtained. Subsequently, in step S1708, the latest X-ray imaging image is obtained. The follow-up observation situation determination unit 1301 obtains the imaging start times included in all the obtained imaging maneuver information and obtains the imaging maneuver information having the imaging start time closest to that of the arrangement objective imaging maneuver information. It should be noted that the imaging start times are obtained for the comparison herein, but any information may be used as long as the imaging order can be determined by using the information. Subsequently, in step S1709, the already-arranged annotation information of the past image is obtained. The follow-up observation situation determination unit 1301 obtains the already-arranged annotation information registered in the past image information included in the latest imaging maneuver information obtained in step S1708. Subsequently, in step S1710, the follow-up observation situation determination unit 1301 obtains all the annotation information included in the already-arranged annotation information and checks whether the follow-up observation annotation in which the setting of the follow-up observation is ON exists. In a case where the follow-up observation annotation does not exists, the follow-up observation situation of the determination objective imaging maneuver information is determined as "no follow-up observation". In a case where the follow-up observation annotation exists, subsequently, in step S1711, it is checked whether a specified period has not elapsed since the imaging time of the latest past image. The specified period indicated herein can be arbitrarily set in the X-ray imaging apparatus. The follow-up observation situation determination unit 1301 compares the imaging start time included in the latest past image information with a current time. In a case where the specified period has elapsed, the follow-up observation situation of the determination objective imaging maneuver information is determined as "no follow-up observation". In a case where the specified period has not elapsed, the follow-up observation situation of the determination objective imaging maneuver information is determined as "follow-up observation in progress". Subsequently, the determination result of the follow-up observation situation is set in the determination objective imaging maneuver information. In a case where the follow-up observation situation is "follow-up observation in progress", in step S1712, the follow-up observation situation determination unit 1301 sets the follow-up observation situation of the determination objective imaging maneuver information as "follow-up observation in progress". In a case where the follow-up observation situation is "no follow-up observation", in step S1713, the follow-up observation situation determination unit 1301 sets the follow-up observation situation of the determination objective imaging maneuver information as "no follow-up observation". Subsequently, in step S1714, the follow-up observation situation determination unit 1301 sets the follow-up observation situation determination state of the determination objective imaging maneuver information as "already determined". Thus far, the follow-up observation situation determination processing for one piece of the determination objective imaging maneuver information is completed. Subsequently, in step S1715, the follow-up observation situation determination unit 1301 checks whether the imaging maneuver information in which the follow-up observation situation determination state is "not yet ended" exists in the same examination information. In a case where the imaging maneuver information exists, the flow is shifted to step S1702, and the similar determination processing is repeated. In a case where the imaging maneuver information does not exist, it is determined that the determination processing is completed for all the imaging maneuver information included in the same examination information, and the flow is shifted to step S1716. Subsequently, in step S1716, the follow-up observation situation determination unit 1301 checks whether the examination information, where the imaging maneuver information in which the follow-up observation situation determination state is "not yet ended" exists in the same examination information, exists in the planned examination information. In a case where the examination information exists, the flow is shifted to step S1701, and the similar determination processing is repeated with respect to the imaging maneuver information included in the examination information. In a case where the examination information does not exist, it is determined that the determination processing is completed for all the imaging maneuver information included in the planned examination information, and the follow-up observation situation determination processing at the time of starting the examination is ended.

Figure 18:
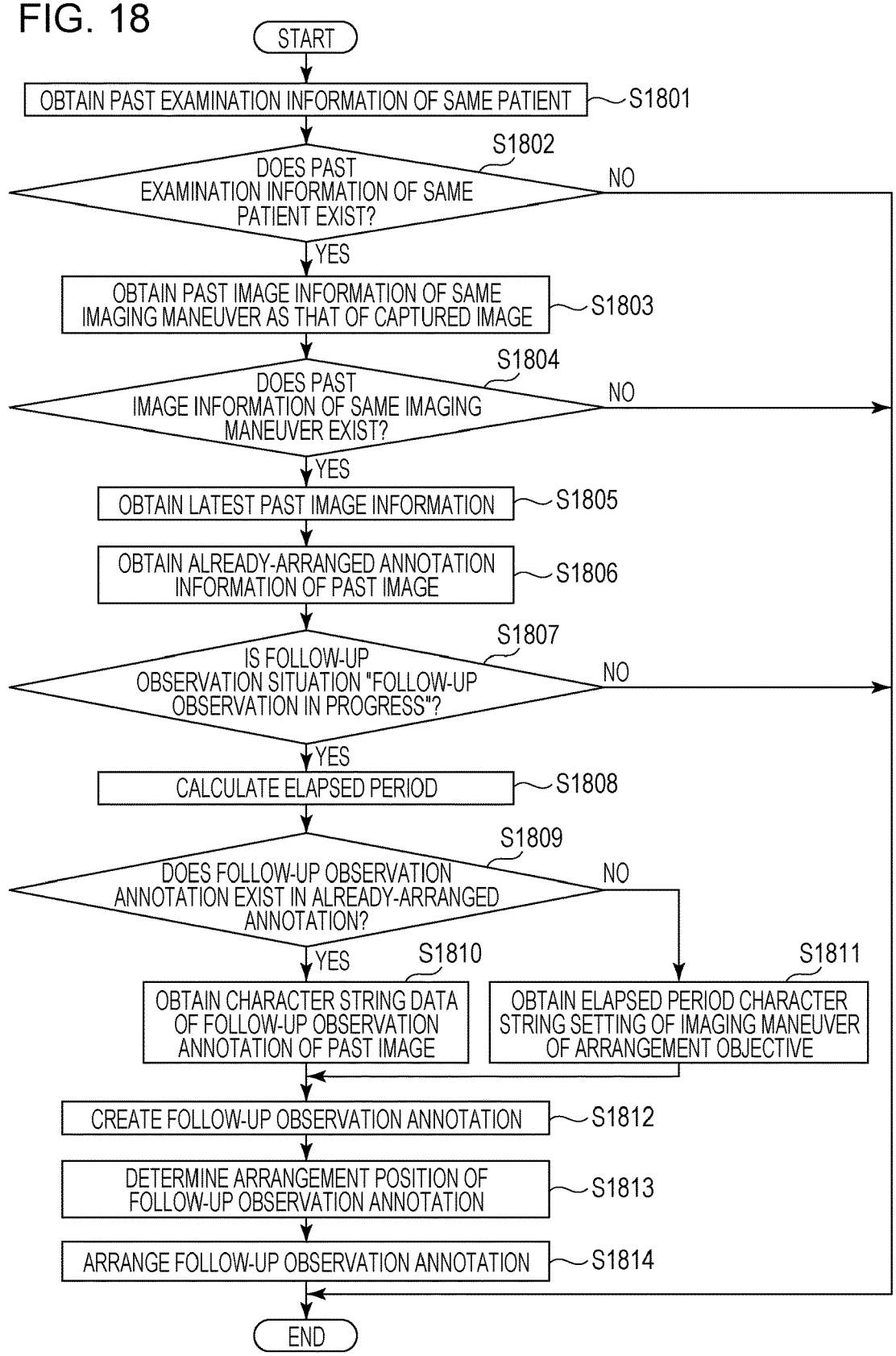
FIG. 18 is a flow chart illustrating a flow of the follow-up observation annotation arrangement processing according to an exemplary embodiment.

Next, a flow of the follow-up observation annotation arrangement processing according to the present exemplary embodiment will be illustrated by using FIG. 18. The flow from step S1801 to step S1806 is similar to that from step S801 to step S806 in FIG. 8. Subsequently, in step S1807, the follow-up observation situation of the imaging maneuver information including the X-ray imaging image of the arrangement objective is checked. The determination unit 305 checks whether the follow-up observation situation included in the imaging maneuver information is "follow-up observation in progress". In a case where the follow-up observation situation is "no follow-up observation", the determination unit 305 determines "no necessity of follow-up observation annotation arrangement". In a case where the follow-up observation situation is "follow-up observation in progress", the determination unit 305 determines "follow-up observation annotation arrangement is necessary". After the determination as to whether the follow-up observation annotation arrangement can be performed, the determination unit 305 transmits the follow-up observation annotation arrangement information to the imaging control unit 306. With the above-described method, it is possible to automatically determine whether the arrangement can be performed on the basis of the follow-up observation situation set for each imaging maneuver. Subsequently, in step S1808, an elapsed period is calculated. The imaging control unit 306 transmits the X-ray imaging image information of the arrangement objective and the latest past image information to the period obtaining unit 304 and instructs the elapsed period measurement. When the elapsed period measurement instruction is received, the period obtaining unit 304 first determines an elapsed period measurement objective time. Subsequently, the period that has elapsed between the elapsed period measurement objective time and the imaging start time of the X-ray imaging image of the arrangement objective. After the elapsed period measurement, the period obtaining unit 304 notifies the imaging control unit 306 of the elapsed period measurement result. Subsequently, in step S1809, it is determined whether the follow-up observation annotation exists in the already-arranged annotation information. The determination unit 305 obtains all the annotation information included in the already-arranged annotation information and checks whether the follow-up observation annotation in which the setting of the follow-up observation is ON exists. In a case where the follow-up observation annotation exists, subsequently, in step S1810, the determination unit 305 obtains the follow-up observation annotation of the follow-up observation annotation included in the past image. In a case where the follow-up observation annotation does not exist, subsequently, in step S1811, the determination unit 305 obtains the follow-up observation annotation set in the arrangement objective imaging maneuver information as the elapsed period character string setting. In this manner, the follow-up observation annotation is followed in a case where the follow-up observation annotation has already been arranged in the past, or the follow-up observation annotation set in the imaging maneuver information is used in a case where the follow-up observation annotation has not been arranged, so that the format of the follow-up observation annotation for each imaging maneuver can be easily unified without depending on the sense of the operator. The flow of the subsequent step S1812 to step S1814 is similar to the flow of step S810 to step S812 in FIG. 8.

Figure 19:
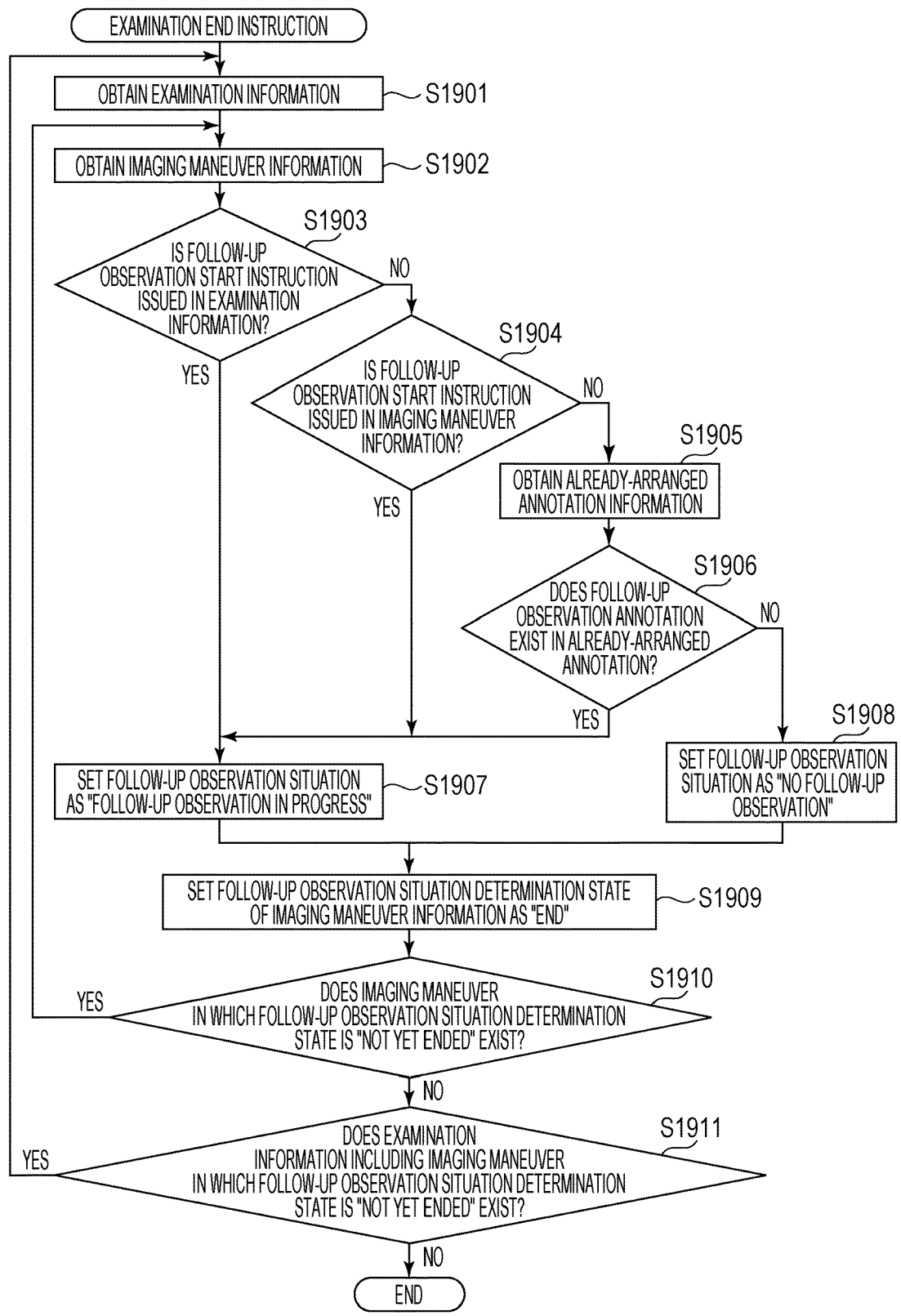
FIG. 19 is a flow chart illustrating a flow of the follow-up observation situation determination processing at the time of the end of the examination according to an exemplary embodiment.

Next, a flow of the follow-up observation situation determination processing at the end of the examination executed in step S1409 in FIG. 14 will be illustrated by using FIG. 19. The flow from step S1901 to step S1904 is similar to the flow from step S1701 to step S1704 illustrated in FIG. 17. In step S1904, in a case where the follow-up observation start instruction is not issued in the determination objective imaging maneuver information, subsequently, in step S1905, the follow-up observation situation determination unit 1301 obtains the already-arranged annotation information registered in the X-ray imaging image information of the arrangement objective. Subsequently, in step S1906, the follow-up observation situation determination unit 1301 obtains all the annotation information included in the already-arranged annotation information and checks whether the follow-up observation annotation in which the setting of the follow-up observation is ON exists. In a case where the follow-up observation annotation does not exist, the follow-up observation situation of the determination objective imaging maneuver information is determined as "no follow-up observation". In a case where the follow-up observation annotation exists, the follow-up observation situation of the determination objective imaging maneuver information is determined as "follow-up observation in progress". Subsequently, the determination result of the follow-up observation situation is set in the determination objective imaging maneuver information. In a case where the follow-up observation situation is "follow-up observation in progress", in step S1907, the follow-up observation situation determination unit 1301 sets the follow-up observation situation of the determination objective imaging maneuver information as "follow-up observation in progress". In a case where the follow-up observation situation is "no follow-up observation", in step S1908, the follow-up observation situation of the determination objective imaging maneuver information is set as "no follow-up observation". The subsequent flow from step S1909 to step S1911 is similar to the flow from step S1714 to step S1716 illustrated in FIG. 17.

According to another exemplary embodiment, with regard to "follow-up observation in progress" corresponding to the information indicating the follow-up observation situation, the first imaging concerning a certain follow-up observation is associated with flag information indicating "follow-up observation start" or "first imaging among follow-up observation imaging", and the last imaging is associated with flag information indicating "follow-up observation end" or "last imaging among follow-up observation imaging". In this case, the information indicating the follow-up observation situation is represented as an integer type value, in which "no follow-up observation" is set as 0, "first imaging" is set as 1, "follow-up observation in progress" is set as 2, and "last imaging" is set as 9. These values are changed in accordance with the situation. The management of the follow-up observation situation is realized by these values.

The information indicating the follow-up observation situation may be associated with the medical image or the imaging information by the operation input. For example, a button, an icon, or an item corresponding to each value indicating the follow-up observation situation is displayed on the imaging screen 701, and each of the medical images is associated with information indicating the follow-up observation in accordance with the selection of the button or the like.

It should be noted that, herein, with regard to the follow-up observation, the user may input the follow-up observation ID in accordance with the pressing operation of the button corresponding to "first imaging". The value input by the user is obtained by a medical image processing apparatus as the follow-up observation ID corresponding to the medical image and associated with the image to be stored in the memory.

According to an exemplary embodiment, in accordance with the pressing operation of the button or the like corresponding to "no follow-up observation" from the button, the icon, or the item displayed on the imaging screen 701, the determination unit 105 determines that the medical image displayed on the imaging screen 701 is not for the follow-up observation. In accordance with the pressing operation of the button or the like corresponding to statuses other than "no follow-up observation", the determination unit 105 determines that the medical image displayed on the imaging screen 701 is for the follow-up observation.

In a case where the plurality of follow-up observations having mutually different purposes are performed, a plurality of follow-up observation IDs concerning this object exist. In this case, when the imaging for the new follow-up observation is performed, which one of the follow-up observation IDs is to be associated is to be selected. According to an exemplary embodiment, the plurality of follow-up observation IDs are displayed, and one of the follow-up observation IDs can be selected by the operation input in accordance with the pressing operation of the button or the like indicating "follow-up observation in progress", and this follow-up observation ID selected by the operation input can be set as the follow-up observation ID of the medical image. According to another exemplary embodiment, in addition to this or instead of this, it is conceivable that the follow-up observation ID may be selected on the basis of a matching degree of the imaging region. In a case where the follow-up observation having the follow-up observation ID of 1 sets a lung field in a chest region as the imaging objective, and the follow-up observation having the follow-up observation ID of 2 sets one of four limbs as the imaging objective, the follow-up observation ID is identified on the basis of the imaging region of the medical image to determine for which one of the follow-up observations the imaging is performed.

In a case where the button or the like corresponding to "last imaging" is selected, the information processing apparatus 101 for medical information may transmit information indicating the last imaging to the image server 104 together with the medical image. Thus, it is possible to notify an image diagnostician who views the image on the image server 104 side that has received this information of the end of the follow-up observation imaging, and also, since a situation is triggered in which the process of the follow-up observation is ended, the management of the medical process can be realized.

As described above, according to the above-described exemplary embodiment, the determination as to whether the follow-up observation annotation can be arranged is performed when the X-ray imaging is executed for the follow-up observation, and in a case where the arrangement is necessary, the elapsed period is calculated to automatically arrange the follow-up observation annotation, so that the burden related to the follow-up observation annotation arrangement can be eliminated. In addition, it is possible to reduce human errors related to the creation of the follow-up observation annotation. In particular, in the case of the follow-up observation, when a treatment such as a surgery is performed with respect to a certain region, a change of a recovery situation over a lapse of time is preferably occasionally checked. In this case, while the X-ray image at a certain time point is set as a reference, the X-ray imaging of the same region is occasionally performed over a lapse of certain time. Subsequently, the X-ray images at the respective time points are compared with one another to check the recovery situation. At this time, to facilitate the comparison, the imaging is carried out while the regions for the imaging of the X-ray images are set to be identical to one another as much as possible. Accordingly, it may be difficult for the user to find out the elapsed period from the reference point in the respective X-ray images at a glance in some cases. Therefore, when the annotations are arranged, the X-ray images have such a significance that the follow-up observations are further facilitated. However, when the elapsed period information such as "post-operation 1 week" or "elapsed 4 weeks" is arranged on the X-ray image as the character string data, it is necessary to determine whether the arrangement of the character string data indicating the elapsed period is needed each time the operator performs the imaging. In addition, in a case where the arrangement of the character string data indicating the elapsed period is needed, if the elapsed period section of the character string data is edited to be arranged after the elapsed period of the captured X-ray images is calculated by searching for the X-ray image set as the reference, much the burden is therefore needed before the arrangement of the character string data. This process is at least partly automated by using the information related to the imaging of the object or the like, and the follow-up observations can be facilitated while the burden of the user is reduced.

It should be noted that, as the imaging for the follow-up observations, for example, a case will be considered where one examination including ten performances of the X-ray imaging in different directions or orientations is performed certain days after a reference day such as an operation day (for example, after 5 days). In this case, the determination unit 105 determines that the information indicating the elapsed period is associated with each of the ten X-ray images respectively obtained by the ten performances of the X-ray imaging. Subsequently, the period obtaining unit 106 obtains character information indicating the elapsed period from this reference time such as "post-operation 5 days". The processing unit 107 associates each of the ten X-ray images the information indicating the elapsed period with. For example, the display control unit 308 displays each of the ten X-ray images on the display unit 209 and also overlaps and displays the information indicating the elapsed period on each of the displayed X-ray images. In the above-described single examination, the operation of associating with the ten X-ray images the information indicating the elapsed period is automated, and it is possible to markedly reduce the burden of the user.

Aspects of the present invention can also be realized while a program that realizes one or more functions of the above-described exemplary embodiment is supplied to a system or an apparatus via a network or a storage medium, and one or more processors in a computer of the system or the apparatus reads out the program to be executed. In addition, the program may be provided by being recorded on a computer-readable recording medium. Aspects of the present invention can also be realized by a circuit that realizes one or more functions (for example, ASIC).

Modes in which the above-described exemplary embodiments are appropriately combined with each other are also included in aspects of the present invention.

According to the above-described exemplary embodiment, the X-ray imaging system is exemplified as the information processing system for the medical information, but the exemplary embodiment may be applied to other medical imaging apparatuses such as MRI, PET, SPECT, or a photoacoustic tomograph.

Accordingly, since the information indicating the elapsed period from the reference time can be appropriately associated with the medical image, it is possible to facilitate the follow-up observation based on the medical image.

While aspects of the present invention have been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-227617, filed Nov. 8, 2014, which is hereby incorporated by reference herein in its entirety.

What is claimed is:

1. An information processing apparatus for medical information, comprising:
   a determination unit configured to determine whether a specific information for a follow-up observation is to be associated with a medical image obtained by imaging of an object based on information related to the imaging of the object;
   a period obtaining unit configured to obtain a character information indicating a period that has elapsed between a reference time concerning the specific information and a time of imaging of the medical image;
   a processing unit configured to associate with the medical image the character information indicating the period as the specific information in a case where the determination unit determines that the specific information is to be associated with the medical image; and
   a display control unit configured to display, on a display unit, the character information indicating the period and the medical image associated with each other by the processing unit,
   wherein, the display control unit displays as the specific information the character information indicating the period, which is associated with the medical image being displayed on the display unit by the processing unit, on the medical image being displayed on the display unit.

2. The information processing apparatus for medical information according to claim 1, further comprising:
   a position obtaining unit configured to obtain information indicating a position at which the character information indicating the period is arranged in the medical image,
   wherein the processing unit associates with the medical image the character information indicating the period and the information indicating the position to be stored in a storage unit.

3. The information processing apparatus for medical information according to claim 1, wherein the display control unit displays the character information indicating the period and the medical image at a same time on a display unit.

4. The information processing apparatus for medical information according to claim 1, wherein the determination unit determines whether specific information is to be associated with a second medical image obtained by imaging of the object that is based on information associated with a first medical image obtained by imaging of the object.

5. The information processing apparatus for medical information according to claim 4, wherein, in a case where the specific information is associated with the first medical image obtained by the imaging of a same region as in the second medical image, the processing unit associates with the medical image the character information indicating a period concerning the second medical image as the specific information.

6. The information processing apparatus for medical information according to claim 1, wherein the determination unit determines whether the specific information is to be associated based on the imaging information associated with the medical image specified before the imaging of the medical image.

7. The information processing apparatus for medical information according to claim 1, wherein
   the display control unit displays a screen for inputting information of the reference time in accordance with a state in which the imaging information is specified for the imaging on a display unit in a case where the imaging information is imaging information for managing the period from the reference time.

8. The information processing apparatus for medical information according to claim 1, further comprising:
   an identification unit configured to identify, in a case where first imaging information associated with the medical image is imaging information for managing the period from the reference time, second imaging information having a follow-up observation ID common to the first imaging information,
   wherein the period obtaining unit obtains a reference time associated with the second imaging information as the reference time associated with the imaging information.

9. The information processing apparatus for medical information according to claim 1, wherein
   the display control unit arranges a plurality of medical images corresponding to plural pieces of imaging information having a common follow-up observation ID to be displayed on a display unit in accordance with an operation input.

10. The information processing apparatus for medical information according to claim 1, further comprising:
    a generation unit configured to generate, in a case where second imaging information having a follow-up observation ID common to a follow-up observation ID included in the first imaging information associated with the medical image exists, a subtraction image of a first medical image corresponding to the first imaging information and a second medical image corresponding to second imaging information.

11. The information processing apparatus for medical information according to claim 1, wherein the processing unit associates first information indicating a first imaging with a medical image corresponding to the first imaging from among a plurality of imaging performances for a follow-up observation and associates second information indicating a last imaging with a medical image corresponding to the last imaging.

12. The information processing apparatus for medical information according to claim 1, further comprising:
   a setting unit configured to set a display format of the period;
   wherein the processing unit associates with the medical image information indicating the display format and the information indicating the period as the specific information.

13. The information processing apparatus for medical information according to claim 1, wherein the processing unit associates with the medical image the specific information by including identification information of the medical image in the specific information.

14. An information processing apparatus for medical information, comprising:
   at least one processor; and
   a memory that stores a program for causing the processor to execute specific processing, the specific processing including
   determining whether specific information for a follow-up observation is to be associated with a medical image obtained by imaging of an object based on information related to the imaging of the object,
   obtaining character information indicating a period that has elapsed between a reference time concerning the specific information and a time of imaging of the medical image,
   associating with the medical image the character information indicating the period as the specific information when it is determined that the specific information is to be associated with the medical image, and
   displaying, on a display unit, the character information indicating the period and the medical image associated with each other in the associating,
   wherein, in the displaying, the character information indicating the period which is associated, in the associating, with the medical image being displayed on the display unit is displayed as the specific information on the medical image being displayed on the display unit.

15. A medical imaging apparatus comprising:
   the information processing apparatus for medical information according to claim 1; and
   a sensor unit configured to obtain the medical image.

16. The medical imaging apparatus according to claim 15, wherein the sensor unit includes a sensor array in which a plurality of pixels are arranged in a matrix and detects X-rays to obtain a two-dimensional image.

17. An information processing method for medical information, comprising:
   determining whether specific information for a follow-up observation is to be associated with a medical image obtained by imaging of an object based on information related to the imaging of the object;
   obtaining information of a reference time concerning the specific information;
   obtaining character information indicating a period that has elapsed between the reference time and a time of imaging of the medical image;
   associating with the medical image the character information indicating the period as the specific information in a case where it is determined that the specific information is to be associated with the medical image; and
   displaying, on a display unit, the character information indicating the period and the medical image associated with each other in the associating,
   wherein, in the displaying, the character information indicating the period which is associated, in the associating, with the medical image being displayed on the display unit is displayed as the specific information on the medical image being displayed on the display unit.

18. A non-transitory recording medium storing a program for causing a computer to execute the information processing method for medical information according to claim 17.

* * * * *